(12) United States Patent
Keall et al.

(10) Patent No.: US 8,396,270 B2
(45) Date of Patent: Mar. 12, 2013

(54) METHOD TO ESTIMATE 3D ABDOMINAL AND THORACIC TUMOR POSITION TO SUBMILLIMETER ACCURACY USING SEQUENTIAL X-RAY IMAGING AND RESPIRATORY MONITORING

(75) Inventors: Paul J. Keall, Greenwich (AU); Per Rugaard Poulsen, Aabyhoej (DK); Byungchul Cho, Anyang (KR)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 262 days.

(21) Appl. No.: 12/932,060

(22) Filed: Feb. 16, 2011

(65) Prior Publication Data

US 2011/0235860 A1  Sep. 29, 2011

Related U.S. Application Data

(60) Provisional application No. 61/338,311, filed on Feb. 16, 2010.

(51) Int. Cl.
*G06K 9/00* (2006.01)
(52) U.S. Cl. .................................................. 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| | | | |
|---|---|---|---|
| 2003/0163037 A1* | 8/2003 | Bladen et al. | 600/424 |
| 2004/0165696 A1* | 8/2004 | Lee | 378/65 |
| 2008/0081991 A1* | 4/2008 | West et al. | 600/425 |

* cited by examiner

*Primary Examiner* — Atiba O Fitzpatrick
(74) *Attorney, Agent, or Firm* — Lumen Patent Firm

(57) ABSTRACT

A method of estimating target motion for image guided radiotherapy (IGRT) systems is provided. The method includes acquiring by a kV imaging system sequential images of a target motion, computing by the kV imaging system from the sequential images an image-based estimation of the target motion expressed in a patient coordinate system, transforming by the kV imaging system the image-based estimation in the patient coordinate system to an estimate in a projection coordinate system, reformulating by the kV imaging system the projection coordinate system in a converging iterative form to force a convergence of the projection coordinate system to output a resolved estimation of the target motion, and displaying by the kV imaging system the resolved estimation of the target motion.

7 Claims, 18 Drawing Sheets

METHOD TO ESTIMATE 3D ABDOMINAL AND THORACIC TUMOR POSITION TO SUBMILLIMETER ACCURACY USING SEQUENTIAL X-RAY IMAGING AND RESPIRATORY MONITORING

CROSS-REFERENCE TO RELATED APPLICATIONS

This application claims priority from U.S. Provisional Patent Application 61/338,311 filed Feb. 16, 2010, which is incorporated herein by reference.

STATEMENT OF GOVERNMENT SPONSORED SUPPORT

This invention was made with Government support under contract NIH/NCI R01 93626 awarded by National Institutes of Health/National Cancer Institute. The Government has certain rights in this invention.

FIELD OF THE INVENTION

The invention relates to target tracing in radiotherapy. More specifically, the invention relates to reformulating estimated target-surrogate model parameters from expressions in the patient coordinates to expressions in the projection coordinates.

BACKGROUND OF THE INVENTION

Three-dimensional knowledge of a moving target during thoracic and abdominal radiotherapy is a key component to managing respiratory tumor motion, applying either motion inclusive, gated, or tracking treatments.

Several image guided radiotherapy (IGRT) systems were designed for the purpose of real-time 3D tumor position monitoring with synchronous stereoscopic imaging capability, such as four room-mounted kV source/detector pairs of the RTRT system and a dual gantry-mounted kV source/detector of the IRIS system.

Continuous real-time x-ray imaging is ideal for direct monitoring of the moving target. Significant imaging dose to the patient, however, is problematic. In an effort to reduce imaging dose to the patient during x-ray image-based tumor tracking, the 3D target position estimation employing an 'internal-external' correlation model was first introduced in synchrony of the CyberKnife system. Using a dual kV imager, the 3D target positions are determined occasionally by synchronous kV image pairs. With such measured 3D target positions and external respiratory signals, internal-external correlation is established which associates the external signal R(t) into each direction of internal target motion T(x, y, z; t), independently in a linear or curvilinear form. This well-established method is widely used clinically.

However, there are other kV imaging systems which do not allow synchronous stereoscopic imaging; the ExacTrac system has a dual kV imager sharing one generator alternately, and linear accelerators (linacs) for IGRT are equipped with a single kV imager rotating with the gantry. These systems are not currently used for respiratory tumor tracking.

What is needed is a general framework of correlation-based 3D target position estimation, which can be applied to synchronously acquired stereoscopic images and also sequentially acquired images, either by a dual kV imager alternately or by a single kV imager rotationally.

SUMMARY OF THE INVENTION

To address the needs in the art, a method of estimating target motion for image guided radiotherapy (IGRT) systems is provided. The method includes acquiring by a kV imaging system sequential images of a target motion, computing by the kV imaging system from the sequential images an image-based estimation of the target motion expressed in a patient coordinate system, transforming by the kV imaging system the image-based estimation in the patient coordinate system to an estimate in a projection coordinate system, reformulating by the kV imaging system the projection coordinate system in a converging iterative form to force a convergence of the projection coordinate system to output a resolved estimation of the target motion, and displaying by the kV imaging system the resolved estimation of the target motion.

According to one aspect of the invention, the target position T(x, y, z) includes an x-direction corresponding to a left-right (LR) orientation in the patient coordinate system, a y-direction corresponding to a superior-inferior (SI) orientation in the patient coordinate system, and a z-direction corresponding to an anterior-posterior (AP) orientation in the patient coordinate system.

In another aspect of the invention, the imager coordinate system includes a kV source located at a kV source to axis distance (SAD), where the axis is the target isocenter, and an imager located at the SAD minus a source to imager distance (SID), where an origin of the imaging coordinate system is coincident with the target isocenter.

In a further aspect of the invention, the kV imaging system can include an alternate stereoscopic sequential imaging system, a rotational monoscopic sequential imaging system, or a synchronous stereoscopic imaging system.

In yet another aspect of the invention, transforming the image-based estimation in the patient coordinate system to an estimate in a projection coordinate system include sequentially applying a counter-clock wise rotation $\phi$ about the z-axis in the patient coordinate system and rotation of $\theta$ around the y-axis in the patient coordinate system, applying a projection into the z' direction of the imager coordinate system, and performing a least squares estimate in the projection coordinate system using the suitably programmed computer.

According to one aspect of the invention, transforming the image-based estimation in the patient coordinate system to an estimate in a projection coordinate system includes reformulating a least-squares estimation of target-surrogate model parameters from expressions in the patient coordinates to expressions in the projection coordinates.

In another aspect of the invention, the target position T(x, y, z) is continuously estimated using a signal R through the correlation between sequential signals $R_i$ and projected marker positions $p_i$ on intermittently acquired kV images, where the signal R is generated by optical respiratory sensors or accelerometers.

BRIEF DESCRIPTION OF THE DRAWINGS

FIG. 1a shows the CyberKnife system has a dual orthogonal kV imaging system in the coplanar plane, FIG. 1b shows the ExacTrac system has a dual kV imaging system in the non-coplanar plane with the angular separation of 60° and FIG. 1c shows a linac for IGRT has a single gantry mounted kV imaging system in the coplanar plane.

FIG. 6a shows a re-plot of the same data shown in FIG. 4a.

FIG. 6b shows pair-wise accuracy comparison of CyberKnife versus ExacTrac for the 1 s mean imaging interval in FIG. 6a, for the 160 dataset, according to one embodiment of the invention.

DETAILED DESCRIPTION

Clinical image guided radiotherapy (IGRT) systems have kV imagers and respiratory monitors, the combination of which provides an 'internal-external' correlation for respiratory-induced tumor motion tracking. The current invention provides a general framework of correlation-based position estimation that is applicable to various imaging configurations, particularly alternate stereoscopic (ExacTrac) or rotational monoscopic (linacs) imaging, where instant 3D target positions cannot be measured. By reformulating the least-squares estimation equation for the correlation model, the necessity to measure 3D target positions from synchronous stereoscopic images can be avoided. The performance of this sequential image-based estimation was evaluated in comparison with a synchronous image-based estimation. Both methods were tested in simulation studies using 160 abdominal/thoracic tumor trajectories and an external respiratory signal dataset. The sequential image-based estimation method (1) had mean 3D errors less than 1 mm at all the imaging intervals studied (0.2, 1, 2, 5 and 10 s), (2) showed minimal dependencies of the accuracy on the geometry and (3) was equal in accuracy to the synchronous image-based estimation method when using the same image input. The sequential image-based estimation method can achieve sub-mm accuracy for commonly used IGRT systems, and is equally accurate and more broadly applicable than the synchronous image-based estimation method.

Figure 1:
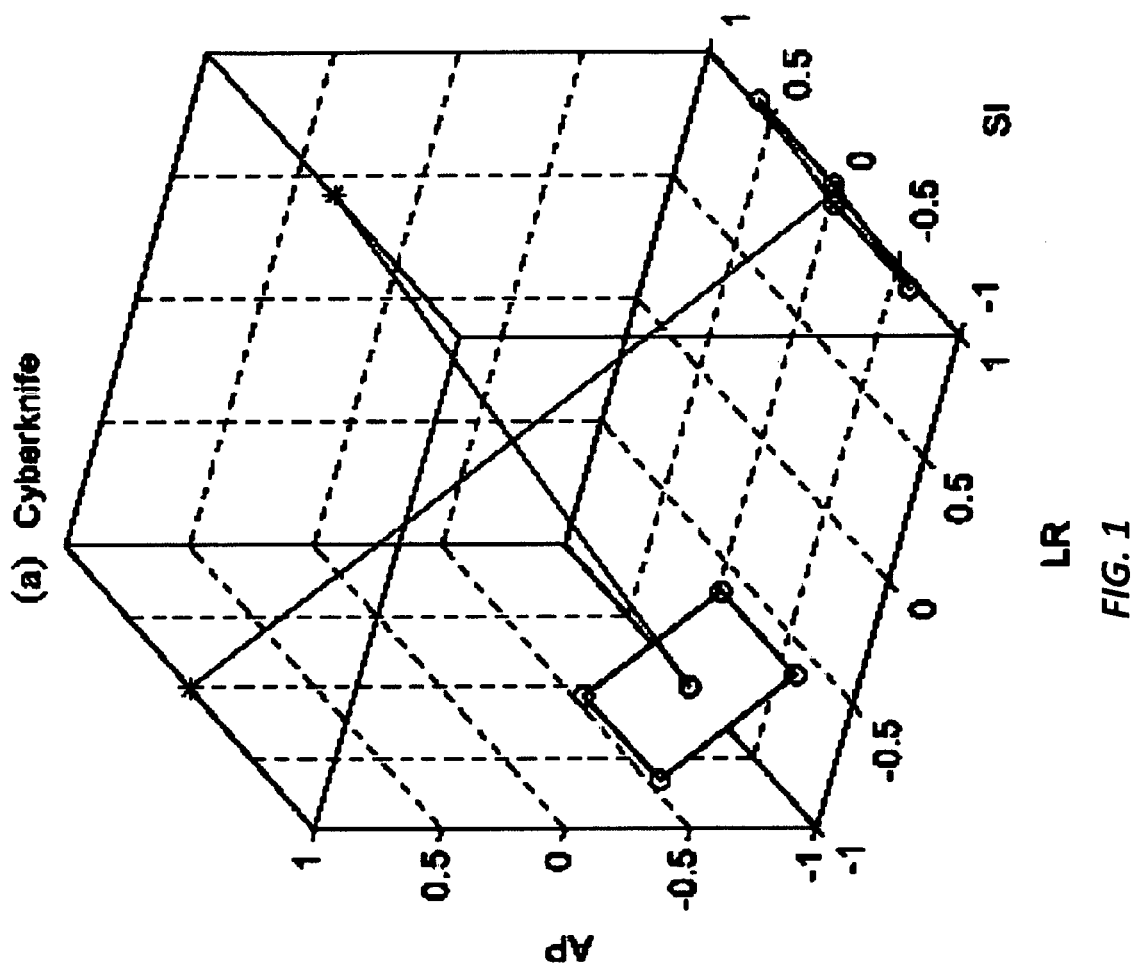
FIGS. 1a-1c show geometries of three kV imaging systems chosen as representative of those commonly used for IGRT.
FIG. 1d shows the rotation transforms from the patient coordinate system (x, y, z) to the imager coordinate system (x', y', z'), according to one embodiment of the invention.
Figure 1:
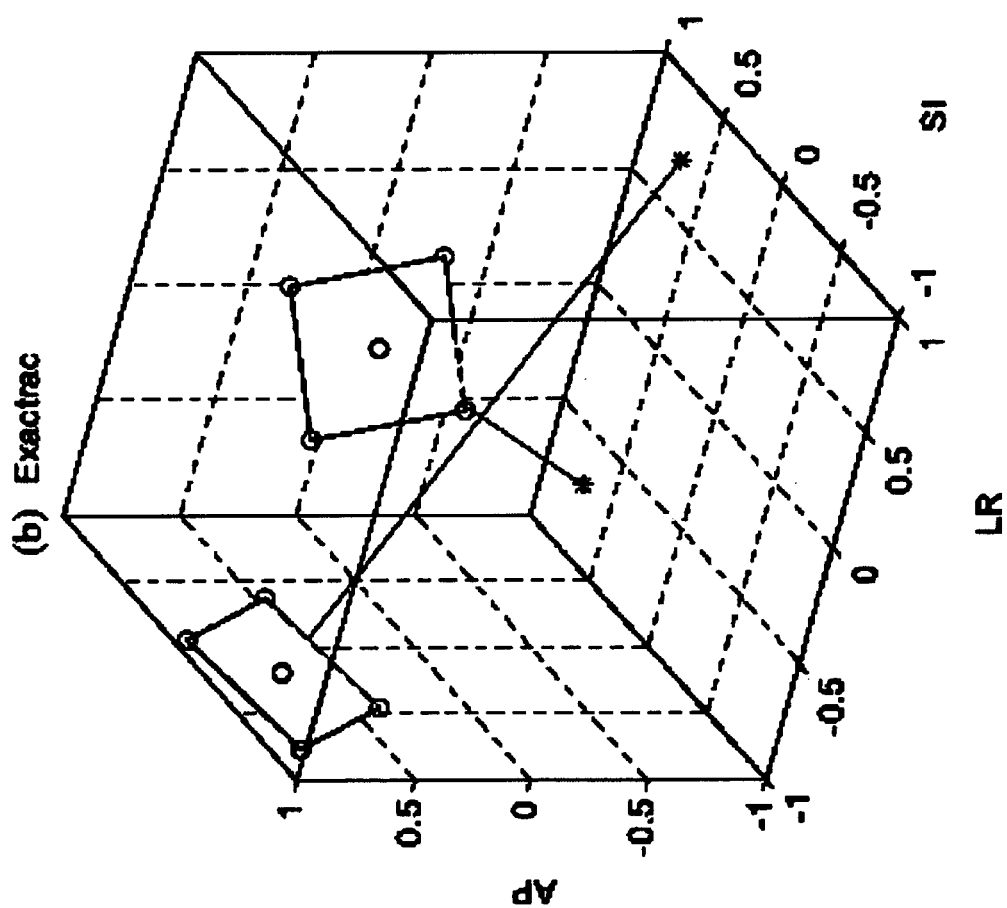
Figure 1:
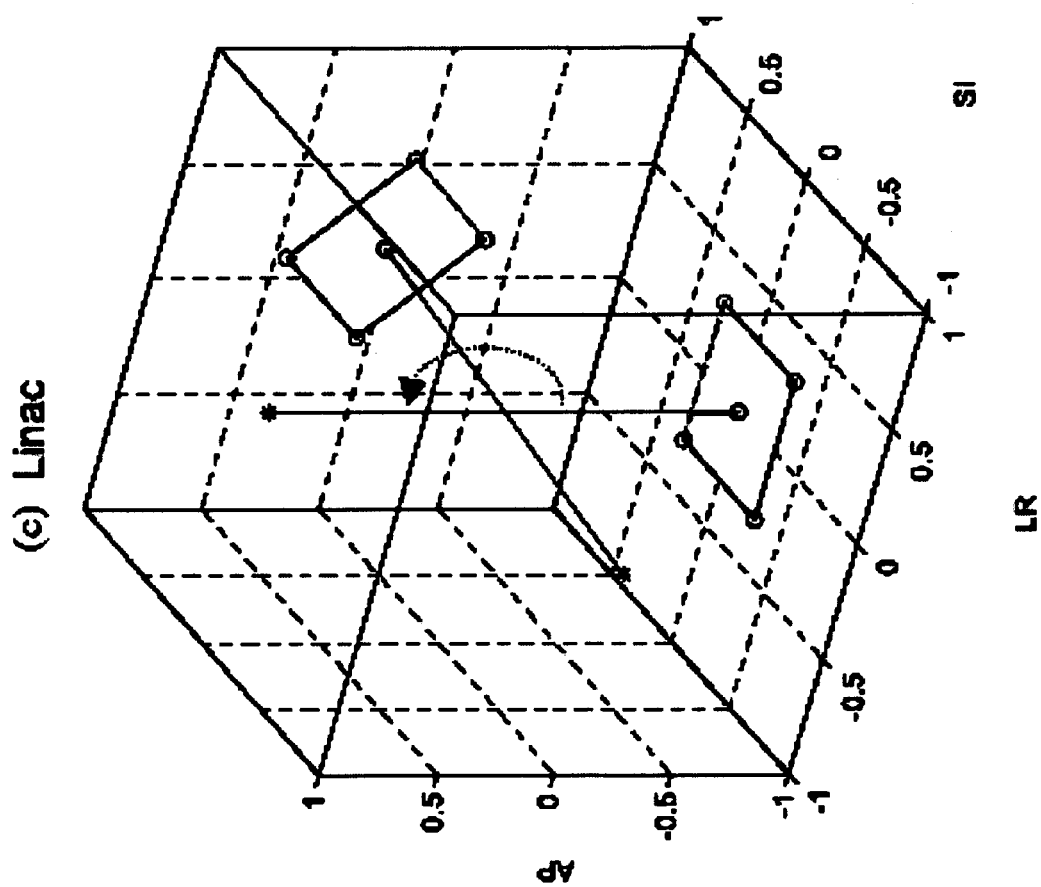
Figure 1:
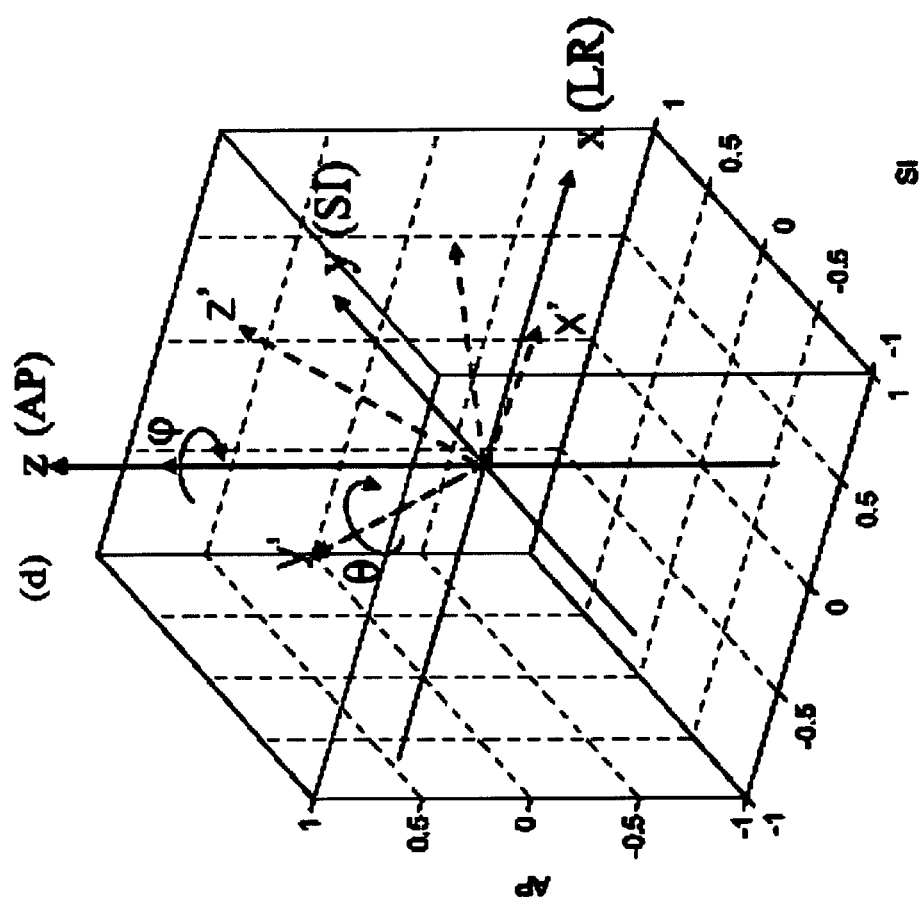

As representatives of the geometries and image acquisition methods among all available IGRT systems, three kV imaging systems are selected: CyberKnife, ExacTrac and linac. Their geometries, image acquisition methods and the estimation approaches used in the examples of the current invention are summarized in Table 1. Details of the geometries are shown in FIGS. 1a-1d, which show geometries of three kV imaging systems chosen as representative of those commonly used for IGRT. FIG. 1a shows the CyberKnife system has a dual orthogonal kV imaging system in the coplanar plane, FIG. 1b shows the ExacTrac system has a dual kV imaging system in the non-coplanar plane with the angular separation of 60° and FIG. 1c shows a linac for IGRT has a single gantry mounted kV imaging system in the coplanar plane. FIG. 1d shows the rotation transforms from the patient coordinate system (x, y, z) to the imager coordinate system (x', y', z'). Rotation of $\phi$ around the z-axis and the following rotation of $\theta$ around the y-axis transforms the patient coordinates into the imager coordinate frame. Note that the source-to-axis distance and source-to-imager distance are not shown in the actual scale (for simplicity), but are included in the calculations.

TABLE 1

The geometries and image acquisition methods of commonly used IGRT systems studied here. The correlation-based 3D target position estimation methods applicable to each image acquisition method are shown in the last column (details are discussed below).

| Commonly used IGRT systems | Geometry (FIG. 1) | Image acquisition method (FIG. 2) | Applicable 3D target position estimation methods |
|---|---|---|---|
| CyberKnife | Coplanar fixed dual kV imager | Synchronous Stereoscopic Imaging | Synchronous image-based estimation or Sequential image-based estimation |
| BrainLab ExacTrac | Non-coplanar fixed dual kV imager with 60° angular separation | Alternate Stereoscopic Imaging | Sequential image-based estimation |
| Elekta, Siemens, Varian linacs | Coplanar rotating single kV imager | Rotational monoscopic imaging | Sequential image-based estimation |

For clarity, the following terms are consistently used throughout this discussion: (1) coplanar and non-coplanar describe the geometric arrangement of single or dual kV imagers, (2) the image acquisition methods are classified into three different categories: synchronous stereoscopic and sequential (either alternate stereoscopic or rotational monoscopic), and (3) the correlation-based 3D target position estimation methods are also classified into synchronous image-based estimation and sequential image-based estimation depending on the image acquisition methods. Synchronous image-based estimation is implemented in the CyberKnife Synchrony system and is used only for comparison in this discussion.

As shown in FIG. 1d, two coordinate systems are used to describe the geometries of three kV imaging systems commonly used for IGRT. The patient coordinate system is defined such that each coordinate of a target position T(x, y, z) corresponds to the left-right (LR), superior-inferior (SI) and anterior-posterior (AP) direction, respectively. The imager coordinate system is defined such that the kV source and detector are located at z'=SAD and z'=SAD−SID, respectively. SAD and SID are the source-to-axis distance and the source-to-imager distance, respectively, where the axis is the target isocenter. The target position T(x, y, z) in the patient coordinates is transformed into a point T'(x', y', z') of the imager coordinate system by sequentially applying a counter-clockwise rotation of $\phi$ around the z-axis and of $\theta$ around the y-axis to the patient coordinate system as follows:

$$\begin{pmatrix} x' \\ y' \\ z' \end{pmatrix} = R_y(\theta)R_z(\varphi)\begin{pmatrix} x \\ y \\ z \end{pmatrix} \qquad (1)$$

$$= \begin{pmatrix} \cos\theta & 0 & \sin\theta \\ 0 & 1 & 0 \\ -\sin\theta & 0 & \cos\theta \end{pmatrix}\begin{pmatrix} \cos\varphi & -\sin\varphi & 0 \\ \sin\varphi & \cos\varphi & 0 \\ 0 & 0 & 1 \end{pmatrix}\begin{pmatrix} x \\ y \\ z \end{pmatrix}$$

$$= \begin{pmatrix} \cos\theta\cos\varphi & -\cos\theta\sin\varphi & \sin\theta \\ \sin\varphi & \cos\varphi & 0 \\ -\sin\theta\cos\varphi & \sin\theta\sin\varphi & \cos\theta \end{pmatrix}\begin{pmatrix} x \\ y \\ z \end{pmatrix}.$$

Further applying a projection into the z' direction of the imager coordinate system, the projected marker position ($x_p$, $y_p$) on the imager plane is given by $$\begin{pmatrix} x_p \\ y_p \end{pmatrix} = \begin{pmatrix} SID/SAD-z' & 0 & 0 \\ 0 & SID/SAD-z' & 0 \end{pmatrix}\begin{pmatrix} x' \\ y' \\ z' \end{pmatrix} \qquad (2)$$

$$= \frac{1}{f(\theta,\varphi)}\begin{pmatrix} \cos\theta\cos\varphi & -\cos\theta\sin\varphi & \sin\theta \\ \sin\varphi & \cos\varphi & 0 \end{pmatrix}\begin{pmatrix} x \\ y \\ z \end{pmatrix}.$$

Figure 2:
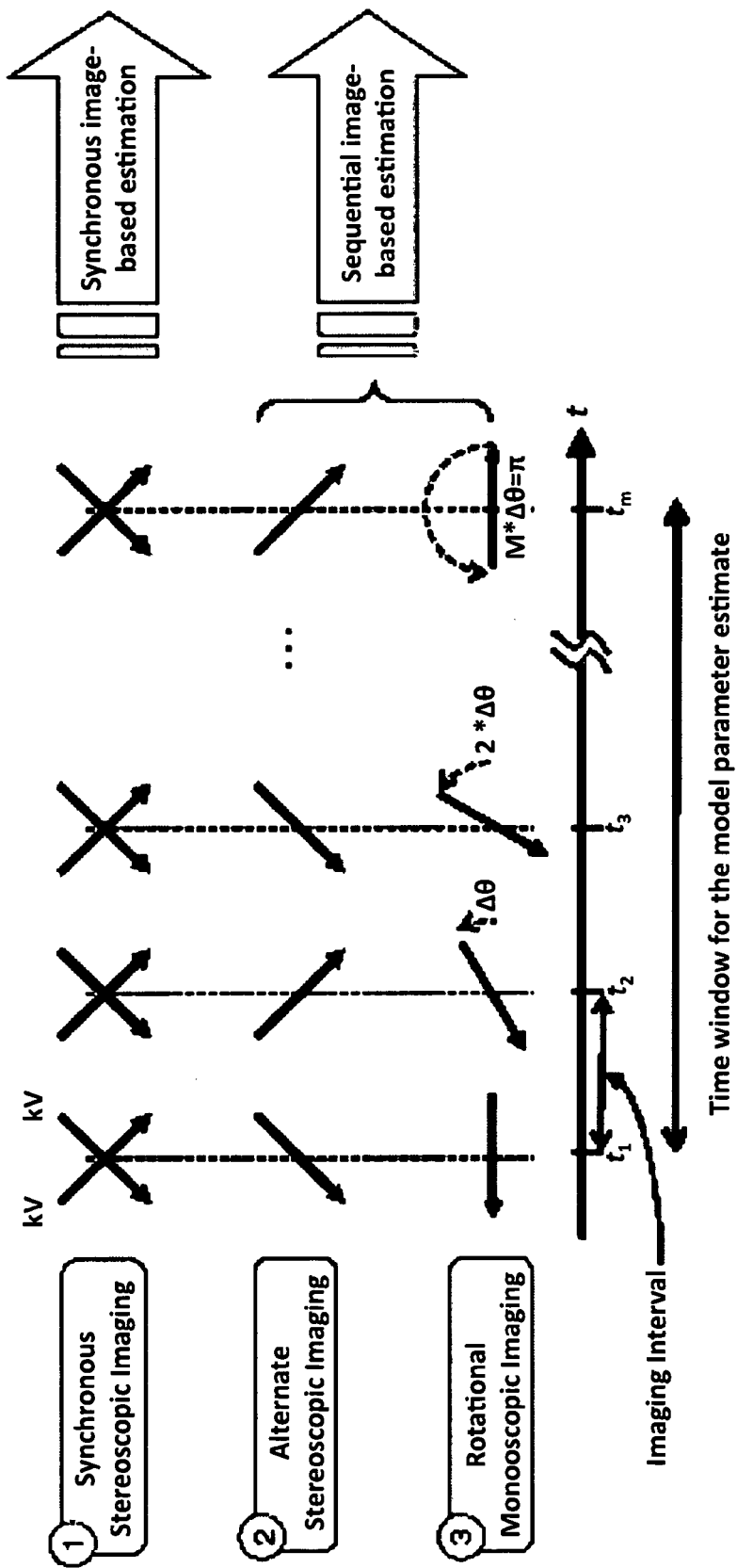
FIG. 2 shows details of the image acquisition method sand estimations according to embodiments of the current invention.

FIG. 2 shows image acquisition methods of commonly used IGRT systems and their estimation methods used in this discussion. The directions of kV imaging and the to angular range of the kV projection images are illustrated with continuous and black-dotted arrows, respectively. Here m is the number of data samples used to estimate the correlation model parameters which is equal to m images for the sequential (either alternate stereoscopic or rotational monoscopic) imaging, but 2m images for the synchronous stereoscopic imaging. Note that a respiratory signal, R(t), is also used in the sequential and synchronous image-based estimations.

Here, the perspective term is $$f(\theta,\varphi) = \frac{SAD - z'(\theta,\varphi)}{SID} \qquad (3)$$

$$= \frac{SAD - [-\sin\theta\cos\varphi \cdot x + \sin\theta\sin\varphi \cdot y + \cos\theta \cdot z]}{SID}.$$

For an internal-external correlation model the linear form is applied, $\hat{T}(t) = aR(t) + b$, $$\begin{pmatrix} \hat{x} \\ \hat{y} \\ \hat{z} \end{pmatrix} = \begin{pmatrix} a_x \\ a_y \\ a_z \end{pmatrix}R(t) + \begin{pmatrix} b_x \\ b_y \\ b_z \end{pmatrix}. \qquad (4)$$

The linear correlation model in this example was chosen to see more clearly any existing effect of the geometries and image acquisition methods on the estimation, instead of making it intricate by adding more parameters with elaborate correlation models. However, the framework introduced here can be equally applied to the other linear correlation models, such as a curvilinear model or a state augmented model.

FIG. 2 shows three different image acquisition methods in commonly used IGRT systems and proposed position estimation strategies, which are described in detail below.

The synchronous stereoscopic imaging systems provide synchronously measured kV image pairs, $p(x_p, y_p; t)$ and $p'(x'_p, y'_p; t)$, which reconstruct an instant 3D position T(x, y, z; t) of a moving target by triangulation:

$$\begin{pmatrix} x_p \\ y_p \end{pmatrix}^{(\theta,\varphi)} \otimes \begin{pmatrix} x'_p \\ y'_p \end{pmatrix}^{(\theta',\varphi')} \xrightarrow{\text{Triangulation}} T\begin{pmatrix} x \\ y \\ z \end{pmatrix}.$$

Given m measured target positions (x, y, z; $\{t_1:t_m\}$) and external monitor signals (R; $\{t_1:t_m\}$) up to the time point $t_m$, the model parameters of the correlation can be determined in a least-squares sense as follows:

$$(\hat{a}, \hat{b}) = \operatorname*{argmin}_{i=1}^{m} \|T(t_i) - (aR(t_i) + b)\|^2. \qquad (5)$$

Since the correlation model is linear in the model parameters, the above minimization problem is converted into the following closed-form matrix equation:

$$\begin{pmatrix} x(t_1) & y(t_1) & z(t_1) \\ \vdots & & \\ x(t_m) & y(t_m) & z(t_m) \end{pmatrix} = \begin{pmatrix} R(t_1) & 1 \\ \vdots & \\ R(t_m) & 1 \end{pmatrix}\begin{pmatrix} a_x & a_b & a_z \\ b_x & b_b & b_z \end{pmatrix}. \qquad (6)$$

With the model parameters given by solving the above equation, the estimated target positions ($\hat{x}$, $\hat{y}$, $\hat{z}$; $t_m \leq t < t_{m+1}$) will be determined from $R(t_m \leq t < t_{m+1})$ using equation (4) until a next synchronous stereoscopic image-pair is acquired at time $t_m + 1$. Once the new target position is determined by triangulation with the image pair, the model parameters are updated by solving equation (6) with the most recently acquired consecutive m target positions and the external monitor signals. In such a way the model can adapt the temporal changes in the correlation. Since equation (6) is expressed in the patient coordinates, the synchronous image-based estimation is irrelevant to the geometry of the two imagers.

Unlike the synchronous image-based estimation solving the correlation model in each patient coordinate after triangulation, the sequential image-based estimation is designed to determine the model parameters directly using the projection positions in the imager coordinate because triangulation is not feasible for sequentially acquired kV images.

Given m projection data p ($x_p(\theta_i, \phi_i)$, $y_p(\theta_i, \phi_i)$; $\{t_1:t_m\}$) measured sequentially at various projection angles of ($\theta_i, \phi_i$) at time $t_i$, the least-squares estimation can be performed in the imager coordinates with equations (1) and (4):

$$(\hat{a}, \hat{b}) = \operatorname*{argmin}_{i=1}^{m} \|p(\theta_i, \varphi_i; t_i) - P(\theta_i, \varphi_i) \cdot (aR(t_i) + b)\|^2. \qquad (7)$$

Here, P ($\theta_i, \phi_i$) represents the whole projection operation including the rotation transforms given in equation (1).

Similar to the synchronous image-based estimation expressed in equations (5) and (6), the above minimization problem is converted into the following matrix equation:

$$\begin{pmatrix} f(\theta_1, \varphi_1) \cdot x_p(\theta_1 \cdot \varphi_1) \\ f(\theta_1, \varphi_1) \cdot y_p(\theta_1 \cdot \varphi_1) \\ \vdots \\ f(\theta_m, \varphi_m) \cdot x_p(\theta_m \cdot \varphi_m) \\ f(\theta_m, \varphi_m) \cdot y_p(\theta_m \cdot \varphi_m) \end{pmatrix} = \qquad (8)$$

$$\begin{pmatrix} \cos\theta_1\cos\varphi_1 \cdot (a_x R(t_1) + b_x) - \cos\theta_1\sin\varphi_1 \cdot (a_y R(t_1) + b_y) + \sin\theta_1 \cdot \\ (a_z R(t_1) + b_z)\sin\varphi_1 \cdot (a_x R(t_1) + b_x) + \cos\varphi_1 \cdot (a_y R(t_1) + b_y) \\ \vdots \\ \cos\theta_m\cos\varphi_m \cdot (a_x R(t_m) + b_x) - \cos\theta_m\sin\varphi_m \cdot (a_y R(t_m) + b_y) + \sin\theta_m \cdot (a_z R(t_m) + b_z)\sin\varphi_m \cdot \\ (a_x R(t_m) + b_x) + \cos\varphi_m \cdot (a_y R(t_m) + b_y) \end{pmatrix} =$$

$$\begin{pmatrix} \cos\theta_1\cos\varphi_1 R(t_1) & \cos\theta_1\cos\varphi_1 & -\cos\theta_1\sin\varphi_1 R(t_1) & -\cos\theta_1\sin\varphi_1 & \sin\theta_1 R(t_1) & \sin\theta_1 \\ \sin\varphi_1 R(t_1) & \sin\varphi_1 & \cos\varphi_1 R(t_1) & \cos\varphi_1 & 0 & 0 \\ & & \vdots & & & \\ \cos\theta_m\cos\varphi_m R(t_m) & \cos\theta_m\cos\varphi_m & -\cos\theta_m\sin\varphi_m R(t_m) & -\cos\theta_m\sin\varphi_m & \sin\theta_m R(t_m) & \sin\theta_m \\ \sin\varphi_m R(t_m) & \sin\varphi_m & \cos\varphi_m R(t_m) & \cos\varphi_m & 0 & 0 \end{pmatrix} \cdot \begin{pmatrix} a_x \\ b_x \\ a_y \\ b_y \\ a_z \\ b_z \end{pmatrix}.$$

Equation (8) is to be solved to determine the model parameters ($a_x$, $b_x$, $a_y$, $b_y$, $a_z$, $b_z$), but apparently it is not solvable in its current form because the perspective term f ($\theta_i$, $\phi_i$) is not determined until the equation has been solved.

However, it can be reasonably approximated in a solvable form as follows.

In general, target positions are not far from the isocenter, i.e. Z'<<SAD, and thus $$f = \frac{SAD - z'}{SID} \approx \frac{SAD}{SID}.$$

At the first approximation, by ignoring the perspective to projection (i.e. assuming parallel projection), equation (8) can be solvable with $$f^{(0)} = \frac{SAD}{SID}.$$

Once the approximate model parameters are determined, the perspective term f ($\theta_i$, $\phi_i$) can be refined by solving equation (8) iteratively as follows (cf equation (3)):

$$f(\theta_i, \varphi_i) \approx \hat{f}^{(k)}(\theta_i, \varphi_i) = \frac{SAD - [-\sin\theta_i\cos\varphi_i \cdot \hat{x}^{(k)}(t_i) + \sin\theta_i\sin\varphi_i \cdot \hat{y}^{(k)}(t_i) + \cos\theta_i \cdot \hat{z}^{(k)}(t_i)]}{SID} \qquad (9)$$

where k is an iteration number and $\hat{x}^{(k)}(t_i) = a_x^{(k)} R(t_i) + b_x^{(k)}$, and so on.

The convergence was tested and the error was found to converge to a minimum, quickly after a few iterations. Therefore, five iterations were used in the example simulations.

Until the next sequential image is given at time $t_m+1$, the estimated target positions ($\hat{x}$, $\hat{y}$, $\hat{z}$; $t_m \leq t < t_{m+1}$) will be determined from $R(t_m \leq t < t_{m+1})$ with the model parameters being computed at time $t_m$. When a new projection position is measured at time $t_m+1$, the model parameters are updated using the most recently acquired consecutive m projection positions and the external monitor signals.

The sequential image-based estimation method was investigated in comparison with the synchronous image-based estimation approach by simulating a variety of scenarios according to the geometries and image acquisition methods of commonly used kV imaging systems.

In the examples, the synchronous and sequential image-based estimations were compared for the three kV imaging systems summarized in Table 1. Next, feasible combinations of the geometries, the image acquisition methods and the estimation methods were further explored for the characterization of the sequential image-based estimation. Each scenario is explained in detail below.

The dataset of total 160 abdominal/thoracic tumor trajectories and associated external respiratory monitor signals acquired with the CyberKnife system was used for these simulations. The tumor trajectories and external respiratory signals were recorded at 25 Hz. The initial 300 s duration of each trajectory was used for simulations with various imaging intervals of 0.2, 1, 2, 5 and 10 s.

Each time a new imaging data was supposed to be acquired, the tumor position was projected into the imager planes for the sequential image-based estimation, using the methods according to the current invention. On the other hand, the tumor position at the moment represented in the patient coordinates was directly used for the synchronous image-based estimation, instead of projection into the imager planes, triangulation and back-transformation into the patient coordinates. That is to say, perfect projection, triangulation and back transformation were assumed in the simulations ignoring any errors.

The most recent 20 consecutive imaging data (which were 3D target positions in the patient coordinates for the synchronous image-based estimation and 2D projected positions in the imager plane for the sequential image-based estimation) were used to determine the correlation model parameters with a moving window. Thus the time windows for the model parameter estimation were 4, 20, 40, 100 and 200 s for the imaging intervals of 0.2, 1, 2, 5 and 10 s, respectively. Note that the 20 3D target positions mean 40 images for the synchronous image-based estimation. Therefore, within the same time window the synchronous image based estimation required twice as many images as the sequential image-based estimation.

The target position estimation started when the first 20 imaging data were acquired. In the sequential image-based estimation, with the first 20 images, the correlation model parameters were calculated iteratively, by applying equations (8) and (9) starting with the initial value of $$f^{(0)} = \frac{SAD}{SID}.$$

After five iterations the computed model parameters were used for retrospective estimation of the target positions from the beginning up to the time point of the 20th image data acquisition. In the synchronous image-based estimation, they were done in the same way except that the model parameters were determined from equation (5) rather than equations (8) and (9).

Later on, whenever a new image was acquired at time $t_m$, the model parameters were updated with the $f(\theta_i, \phi_i)$ value estimated using the previous correlation model parameters. These updated model parameters were used to estimate the target positions prospectively with $R(t_m \leq t < t_{m+1})$, from the current imaging time $t_m$ to the next imaging time $t_{m+1}$.

For simplicity, experimental errors associated with the finite pixel size of the imagers and other intrinsic factors (e.g. geometric calibration of the imagers) were not considered in the simulations. The number of samples for the model parameter estimation was fixed to m=20, which may not be optimal, but is expected to be enough to determine the six model parameters and have little impact on the estimation accuracy. A more relevant factor is the time window because it determines the response time of the model to the temporal change in the internal-external correlation.

The accuracy of the position estimation was quantified by the root-mean-square error (RMSE) for each trajectory as follows:

$$RMSE = \sqrt{\frac{1}{N} \sum_{i=1}^{N} (\hat{x}_i - x_i)^2},$$

and similarly for the y and z components. Here, N is the total number of the estimated data points based on the external signals at 25 Hz for the 300 s duration including the initial 4-200 s with model building. The RMSE was calculated for each of the motion components (LR, SI and AP) and for the 3D vector.

Simulations of 3D target position estimation were performed with the 160 trajectories for the three representative kV imaging systems based on their geometries and image acquisition methods.

(a) CyberKnife system: synchronous stereoscopic imaging with two orthogonal imagers in the coplanar geometry.

The CyberKnife imaging system includes two kV sources at the ceiling and two corresponding flat panel detectors at the floor. The detectors are situated at approximately 140 cm from the isocenter and at a 45° angle to the kV beam central axes. The kV sources are located at 220 cm from the isocenter. Thus SAD and SID were set at 220 and 360 cm, respectively. The geometric configuration of each kV source corresponds to ($\theta_1$=45°, $\phi_1$=0°) and ($\theta_2$=45°, $\phi_2$=0°) in equation (1), respectively. Their orthogonal beam axes form a coplanar plane. However, since the experimental uncertainties were not taken into account for the simulations, each time a new synchronous kV image pair was supposed to be acquired, the true target position in the patient coordinates was directly used instead of projection and triangulation. The synchronous image-based estimation was applied to compute the model parameters with the most recent 20 target positions. Note that in the example, the CyberKnife geometry was used to model both synchronous stereoscopic and alternate stereoscopic image-based estimation.

(b) ExacTrac system: alternate stereoscopic imaging between two imagers with 60° separation in the non-coplanar geometry.

The ExacTrac system includes two kV sources at the floor and two corresponding flat panel detectors at the ceiling. Their beam axes form a non-coplanar plane with 60° angular separation. A projected marker position p was acquired alternately between the two kV imagers configured at ($\theta_1$=135°, $\phi_1$=45°) and ($\theta_2$=135°, $\phi_2$=135°) in equation (1), with SAD=230 cm and SID=360 cm. The sequential image-based estimation was applied to determine and update the correlation parameters with the most recent 20 projection positions.

(c) Linacs: rotational monoscopic imaging with a single imager rotating with the gantry in the coplanar geometry.

Linacs for IGRT are equipped with a single kV imaging system rotating with the gantry. Its rotating beam axes form a coplanar plane. Unlike the real systems, the imager was kept rotating over the 300 s tracking interval with unlimited speed. The 20 consecutive projected positions p were acquired at $\phi$=0° and $\theta_i$=($\pi \cdot i$)/m, i=1, . . . , m, so that the 20 projections covered 180° angular range evenly, to make the mean angular separation 90°. In reality linacs have the upper rotating speed limit of 6° s$^{-1}$. When this limitation is applied, the 20 projections will cover 24, 120, 240, 600 and 1200° for imaging intervals of 0.2, 1, 2, 5 and 10 s, respectively. However, since this inter-relationship between the imaging interval and the angular range is specific only to the linacs' imaging configuration, the angular range was fixed to cover 180° in order to closely investigate the influence of the estimation method itself (sequential versus synchronous) without any influence from the variation of the angular range. The influence from the angular range was separately investigated and presented below. SAD and SID were set at 100 and 150 cm, respectively. The sequential image-based estimation was also applied to this case.

Note that the sequential image-based estimation method of the current invention can also be applicable to the synchronous stereoscopic imaging by bypassing the triangulation procedure. Therefore applying both estimation methods to the same synchronous stereoscopic imaging data provides an important comparison. To test any loss of estimation accuracy of the sequential image-based estimation due to abandoning the privileged synchrony information between images, the approach was applied to the synchronous stereoscopic imaging in the CyberKnife's coplanar and the ExacTrac's non-coplanar geometry, and its estimation errors were compared with the estimation errors of the synchronous image-based estimation.

The synchronous stereoscopic imaging is irrelevant to the geometries, either coplanar or non-coplanar. In contrast, since the sequential image-based estimation may be affected by the geometries, it was tested with the alternate stereoscopic imaging in the CyberKnife's coplanar and ExacTrac's non-coplanar geometries at various imaging intervals.

Another question was the dependence of the sequential image-based estimation on SAD. For this purpose, the sequential image-based estimation for the rotational monoscopic imaging at the 1 s interval was simulated with SAD=100, 150, 200 and 250 cm.

For the rotational monoscopic imaging in the overall comparison described above, the angular range to estimate the model parameters was set at 180° such that the images had a 90° angular separation on average, which would be comparable to the other imaging geometries: 90° separation for the CyberKnife system and 60° separation for the ExacTrac system. One interesting question was how the angular range for the parameter estimation impacted the accuracy of the sequential image-based estimation. Thus simulations were performed with the sequential image-based estimation for the rotational monoscopic imaging in the linacs' coplanar geometry as a function of the angular span.

Figure 3:
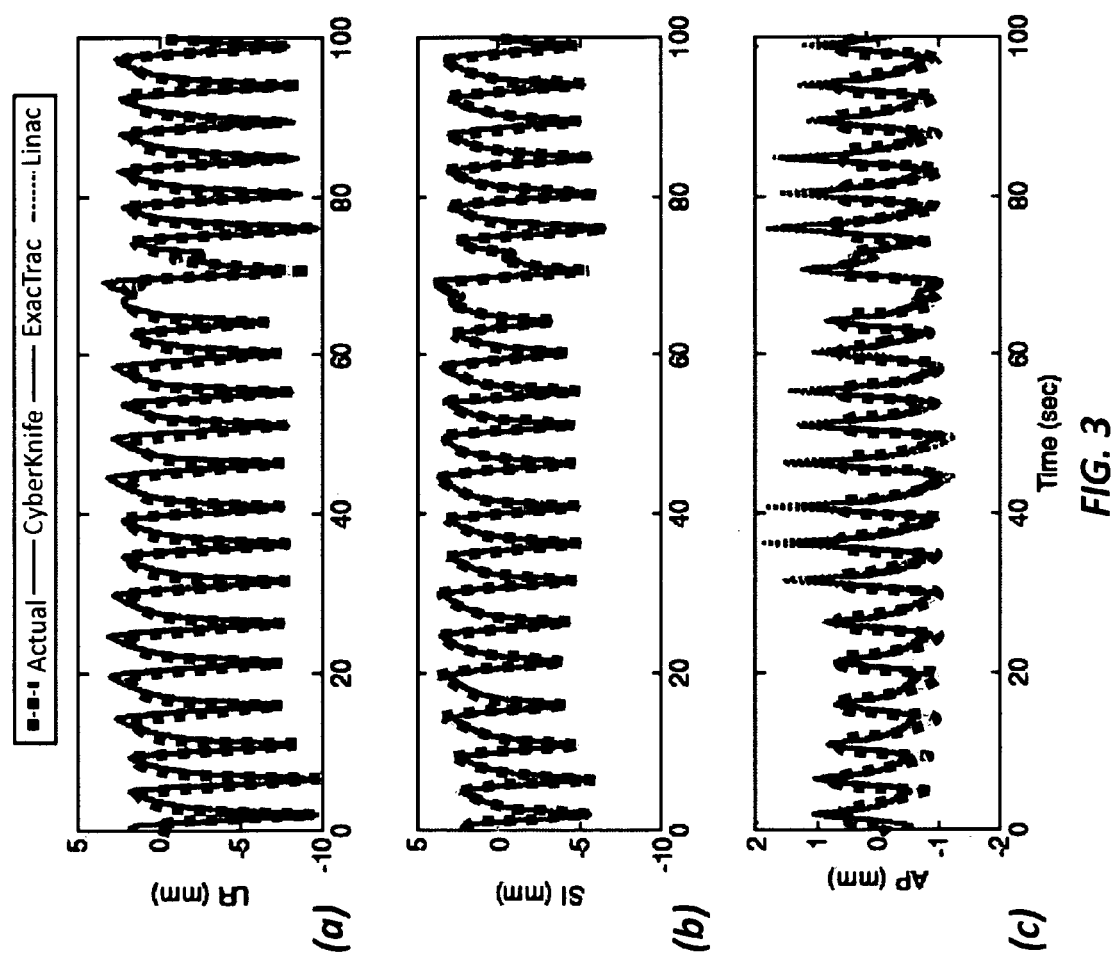
FIGS. 3a-3c show typical tumor motion estimation results for the CyberKnife geometry (synchronous image-based method), ExacTrac and linac geometries (sequential image-based method), respectively, according to one embodiment of the invention.

Typical tumor motion and the corresponding motion estimation traces for the CyberKnife, ExacTrac and linac geometries are shown in FIGS. 3a-3c. The estimated traces are all very similar, even in places where they differ from the tumor motion trace. This similarity means that the limiting factor in this case is not the IGRT system geometry but limitations in the model itself, or the underlying unaccounted-for variations in the intrinsic internal-external correlation, where FIG. 3a shows left-right; FIG. 3b shows superior-inferior, and FIG. 3c shows anterior-posterior. The estimation results are similar for all methods. The kV imaging frequency was one image per second.

FIGS. 4a-4d show the mean estimation RMSE of the estimation method applied to the 160 traces for the three IGRT geometries, according to one embodiment of the current invention. The synchronous image-based estimation was applied to the synchronous stereoscopic imaging in the coplanar geometry (CyberKnife), while the sequential image-based estimation was applied to the alternate stereoscopic imaging in the non-coplanar geometry (ExacTrac) and the rotational monoscopic imaging in the coplanar geometry (linac). Note that these results are not necessarily representative of clinically available system performance, but they represent the potential capability of the systems using the models described.

Figure 4:
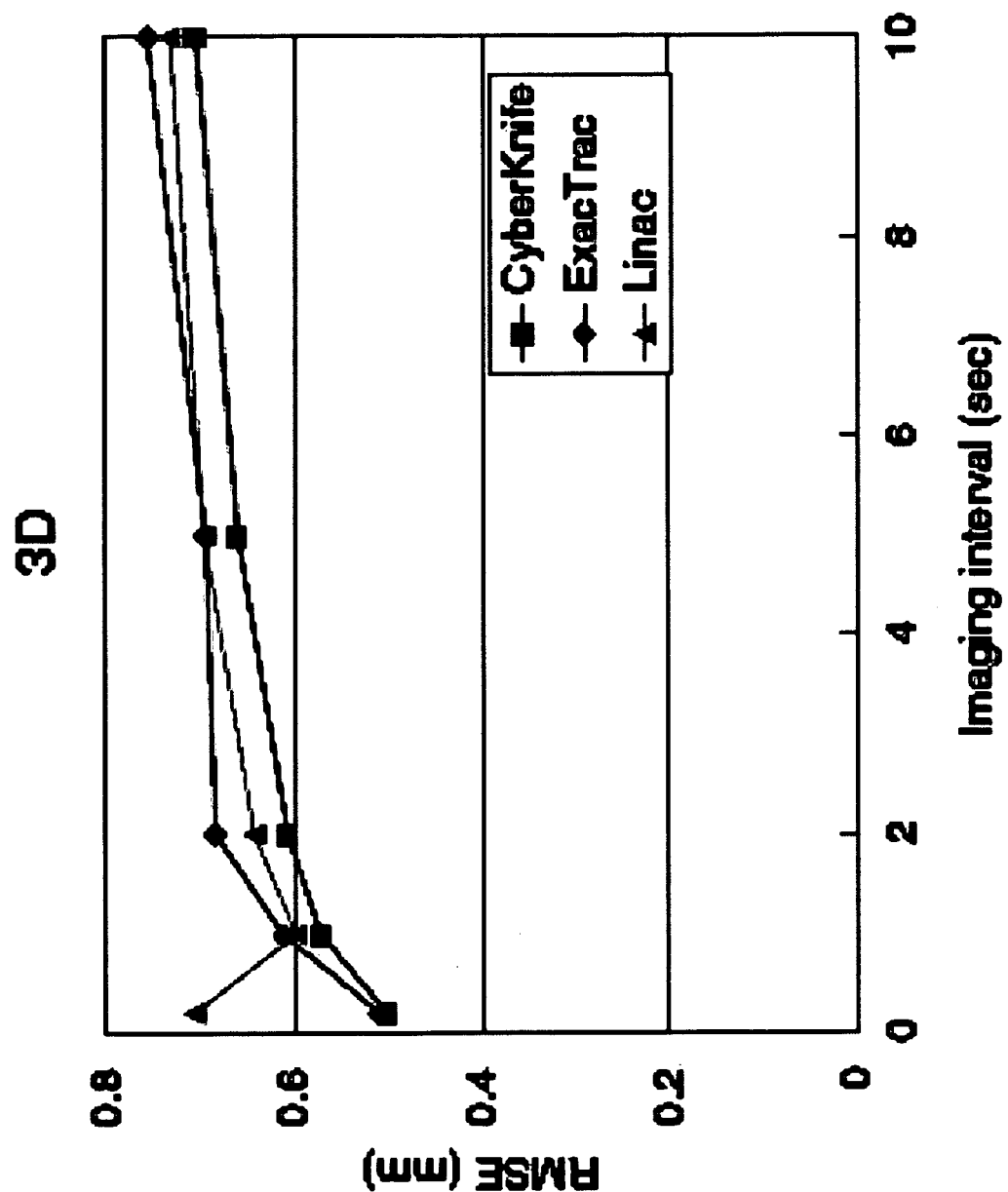
FIGS. 4a-4d show the mean estimation RMSE of the estimation method applied to the 160 traces for the three IGRT geometries, according to one embodiment of the current invention.
Figure 4:
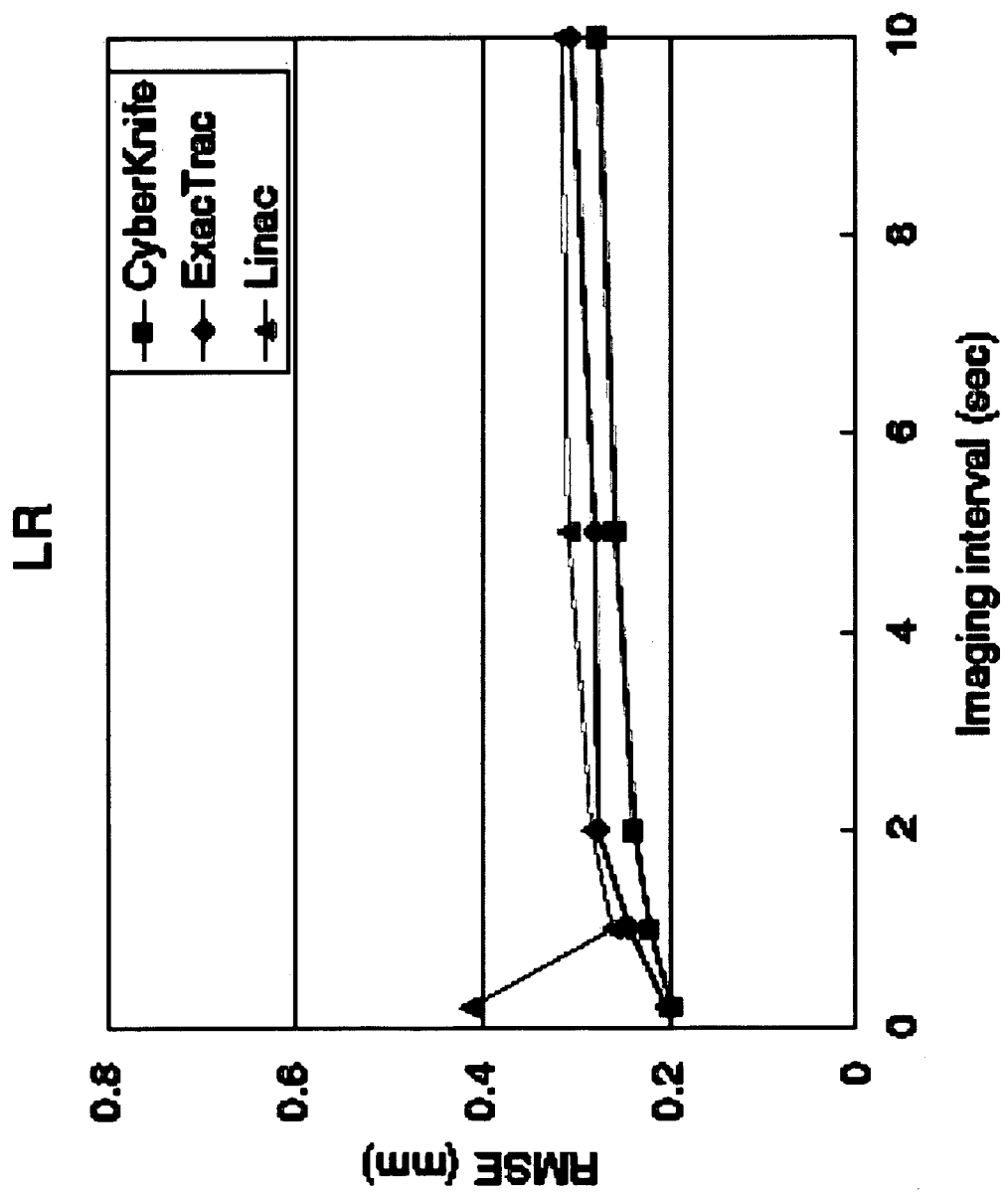
Figure 4:
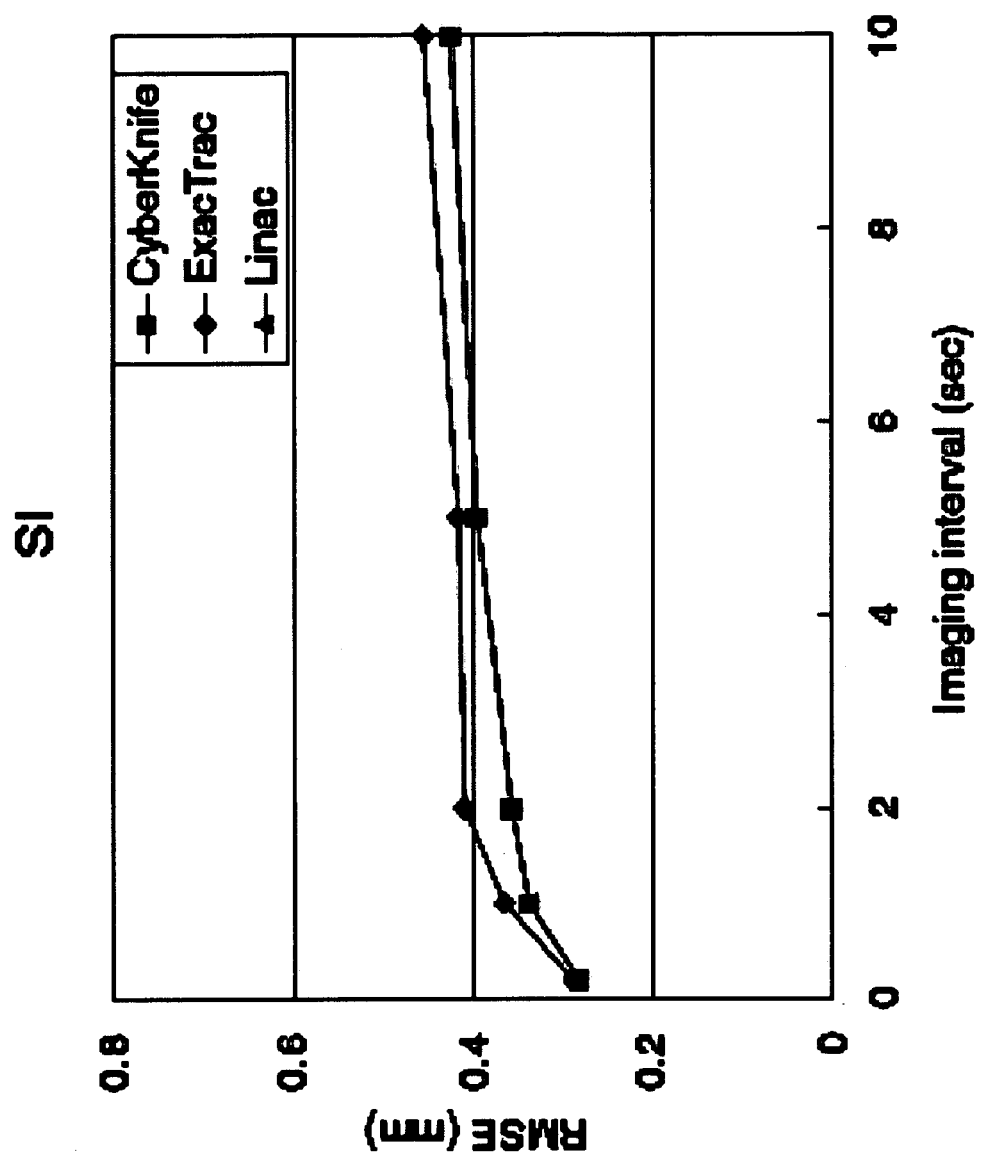
Figure 4:
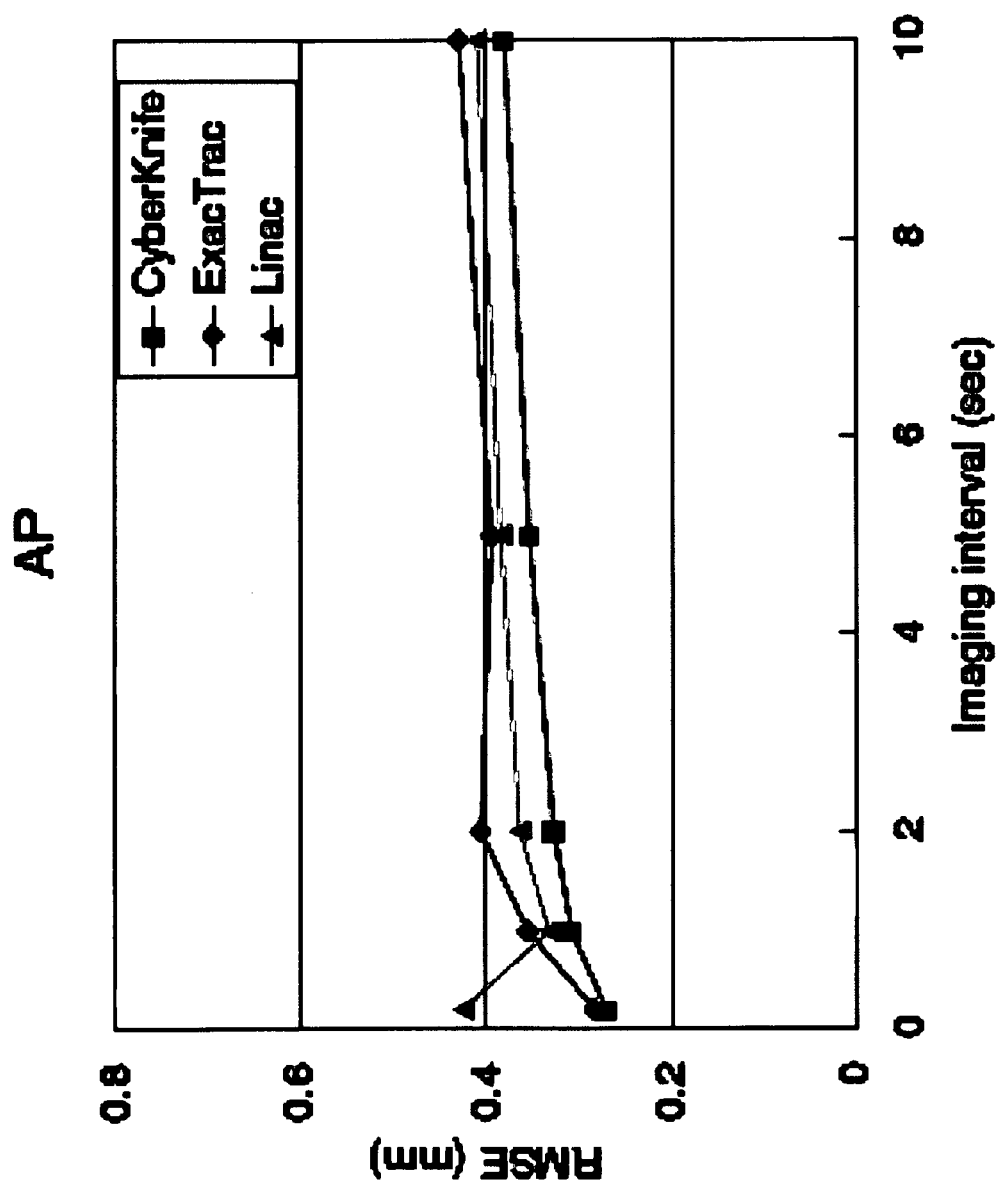

As shown in FIG. 4a, both sequential and synchronous estimation methods can achieve mean 3D errors less than 1 mm for all three imaging systems at all imaging intervals. When the imaging interval approaches zero the estimation error approaches the minimum of ~0.5 mm, which is attributed to the nature of the internal-external correlation that cannot be fully explained by a simple linear function. A longer imaging interval increases the estimation error gradually because the wider time window for the model parameters estimation slows down the model adaptation to the temporal change in the correlation. This response delay of the model adaptation adds ~0.2 mm on the 3D estimation error up to the 10 s imaging interval with the 200 s time window. It suggests that the internal-external correlation does not change rapidly for most cases.

The CyberKnife system shows the best accuracy over all the imaging intervals. Note that the CyberKnife system has double the amount of kV images compared to the others, because the synchronous image-pair is acquired at each imaging interval. Better accuracies of the CyberKnife system in the LR and AP directions, shown in FIGS. 4b-4d, are attributed to this fact because it has double the amount of spatial information in both directions. In contrast, there is no accuracy improvement of the CyberKnife system in the SI direction compared to the linacs' imaging system, which has the same coplanar geometry, as two images acquired at the same time give the identical SI position. In FIG. 4c, the noncoplanar alternate stereoscopic imaging of the ExacTrac system shows lower accuracy in the SI direction compared to the coplanar rotational monoscopic imaging of Linacs, because its non-coplanar geometry projects the SI and LR components onto $y_p$, as shown in the equation (1), while the coplanar geometry of the Linacs estimates the SI component from $y_p$ separately.

One interesting feature of the rotational monoscopic imaging is that the estimation error rebounds at the 0.2 s imaging interval. While the alternate stereoscopic imaging has a 60° angular separation between subsequent images, the rotational monoscopic imaging only has 9° angular separation between subsequent images (180°/20 images). This may not be enough to discriminate small displacement of the target during the short interval of 0.2 s. This fact was confirmed with another simulation in which the angular separation between rotational monoscopic images was 60°. The results (not shown here) did not show an accuracy reduction for 0.2 s imaging intervals. It was also confirmed that the accuracy could be improved by increasing the modeling time window, yet not significantly because the wider window reduced the prompt model adaptation to the temporal change in the correlation. Anyhow, the angular range of 180° during 20 s is impossible considering the speed limit of linacs and such a fast imaging like 0.2 s is unnecessary for the application of the 'internal-external' correlation based target position estimation. However, as it revealed below, the angular range larger than 120° did not affect the estimation accuracy and thus the result of the simulation ignoring the rotating speed limit of linacs might remain valid except the imaging interval of 0.2 s.

Figure 5:
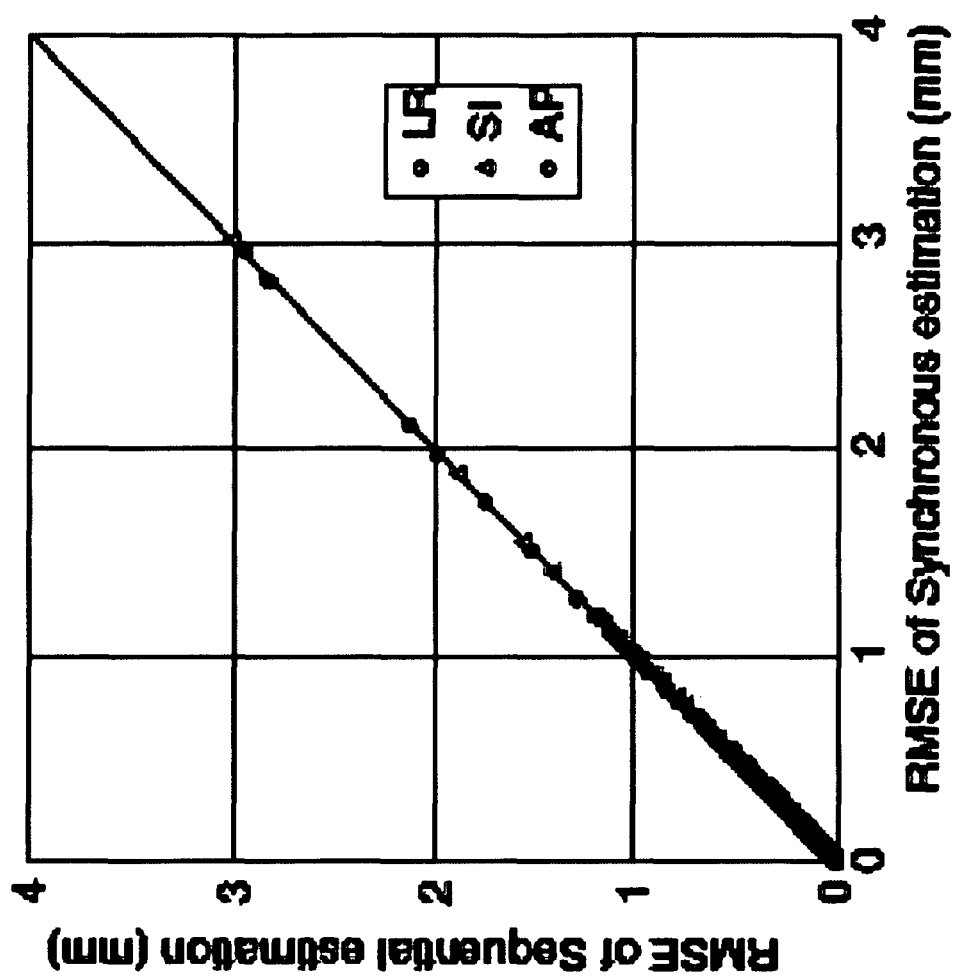
FIG. 5 shows performance comparison of synchronous versus sequential image-based estimation applied to the same synchronous stereoscopic imaging data (1 s interval) in the non-coplanar geometry, according to one embodiment of the invention.

FIG. 5 shows performance comparison of synchronous versus sequential image-based estimation applied to the same synchronous stereoscopic imaging data (1 s interval) in the non-coplanar geometry, according to one embodiment of the invention. Each point represents pair-wise estimation errors of synchronous versus sequential image-based estimation for the 160 trajectories.

The sequential image-based estimation (equation (7)) applied to the synchronous stereoscopic acquisition method of the current invention reveals the same accuracy as the synchronous image-based estimation (equation (5)) over all the image intervals. As an example, the estimation results of the 1 s imaging interval in the non-coplanar geometry are shown in FIG. 5.

The estimation results in the coplanar geometry are also the same, demonstrating no loss of estimation accuracy due to bypassing the triangulation procedure. It means that, at least for the purpose of estimating the internal-external correlation model parameters, the synchronous information on images does not play any role. The practical significances of this fact are: (1) the current sequential form of the ExacTrac system is sufficient for the correlation based target tracking and thus updating the synchronous stereoscopic imaging system is not necessary, and (2) the CyberKnife system can use the sequential image-based estimation with alternate stereoscopic imaging, if necessary, without loss of accuracy. This result implies that the sequential method is equally accurate to the synchronous method and applicable to other IGRT systems, whereas the synchronous method is not.

Figure 6:
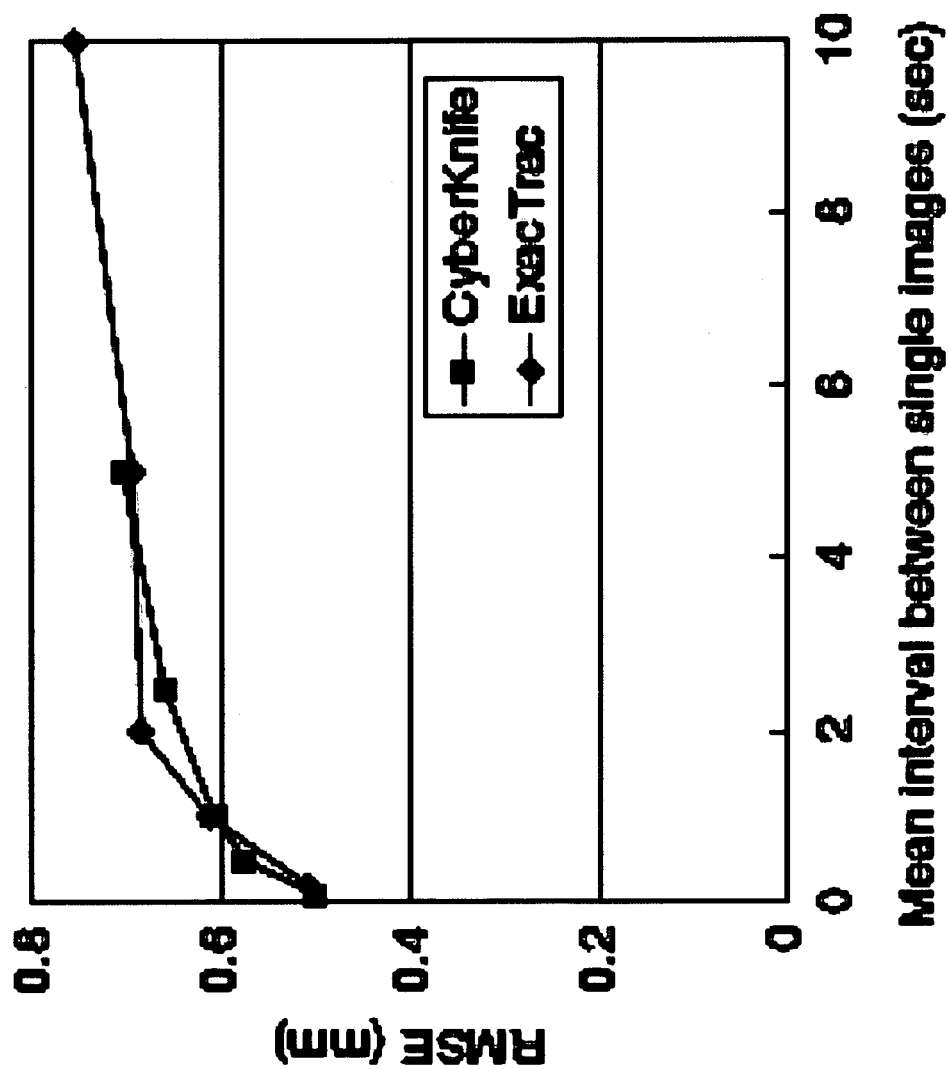
Figure 6:
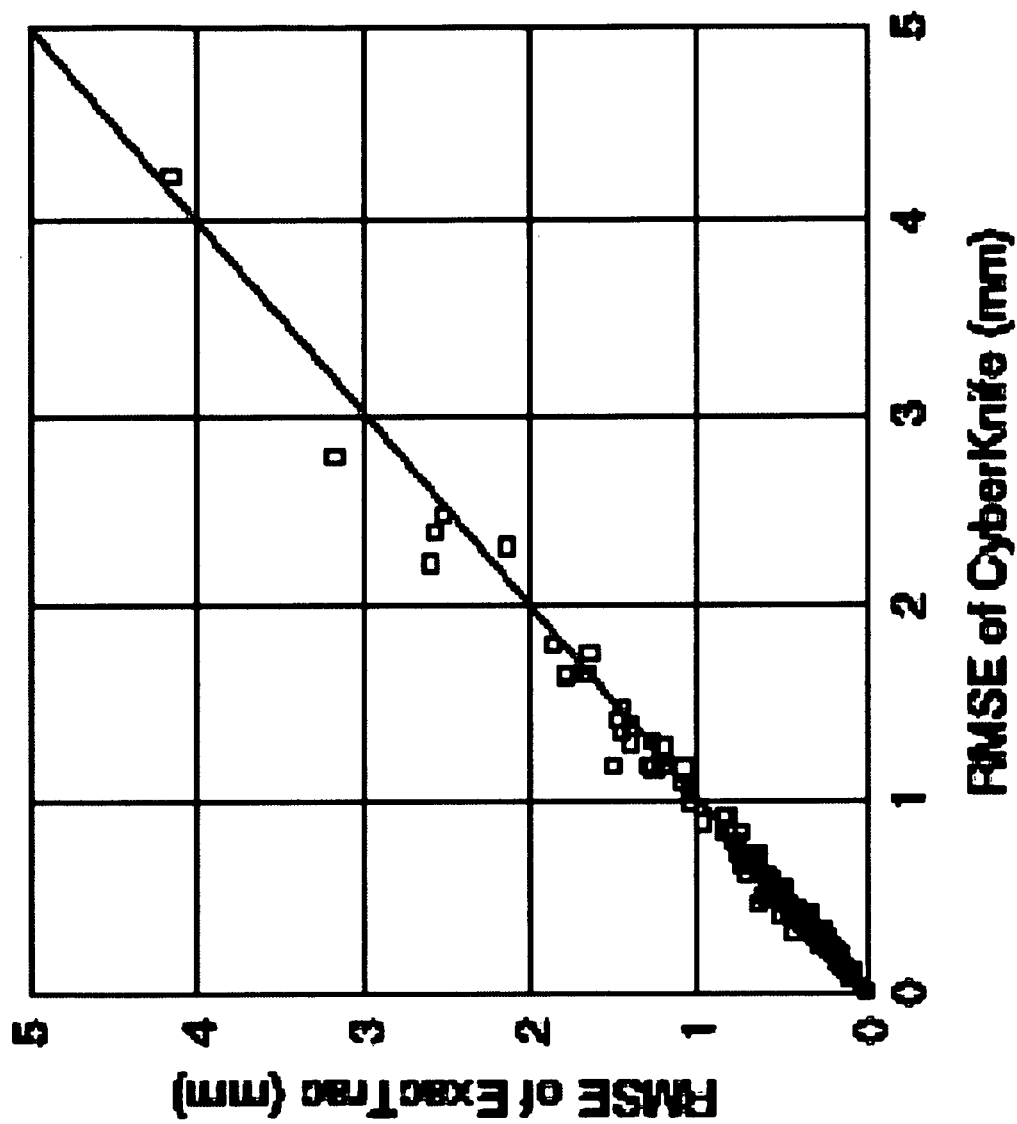

Indeed, the synchronous stereoscopic imaging may not be optimal compared with the alternate stereoscopic imaging if imaging dose to the patient is considered. Acquiring each image alternately at a certain imaging interval may be more accurate than acquiring each synchronous image-pair at a twice longer interval because the former would collect more information on the temporal variation in the internal-external correlation. FIG. 6 is a re-plot of the same data shown in FIG. 4a by rescaling the imaging interval of the synchronous stereoscopic imaging (CyberKnife) such that the number of images are the same as that of the alternate stereoscopic imaging (ExacTrac). However, there is no noticeable accuracy difference between the two approaches. As mentioned earlier, the accuracy of the 3D position estimation was deteriorated less than 0.2 mm by increasing the imaging interval from 0.2 to 10 s probably due to the slow change of the internal-external correlation over time. In other words, the 0.2 mm gain of the tracking accuracy cannot be justified at the cost of 20 times more imaging dose to the patient within the imaging interval studied. In addition, all the three image acquisition methods provide already sub-mm accuracy with only subtle difference, thus there is no method superior to another.

FIG. 6a shows a re-plot of the 3D mean RMSE from FIG. 4a by rescaling the imaging interval of the synchronous stereoscopic imaging (CyberKnife) such that the number of images are the same as that of the alternate stereoscopic imaging (ExacTrac). FIG. 6b shows pair-wise accuracy comparison of CyberKnife versus ExacTrac for the 1 s mean imaging interval in FIG. 6a, for the 160 dataset.

Figure 7A:
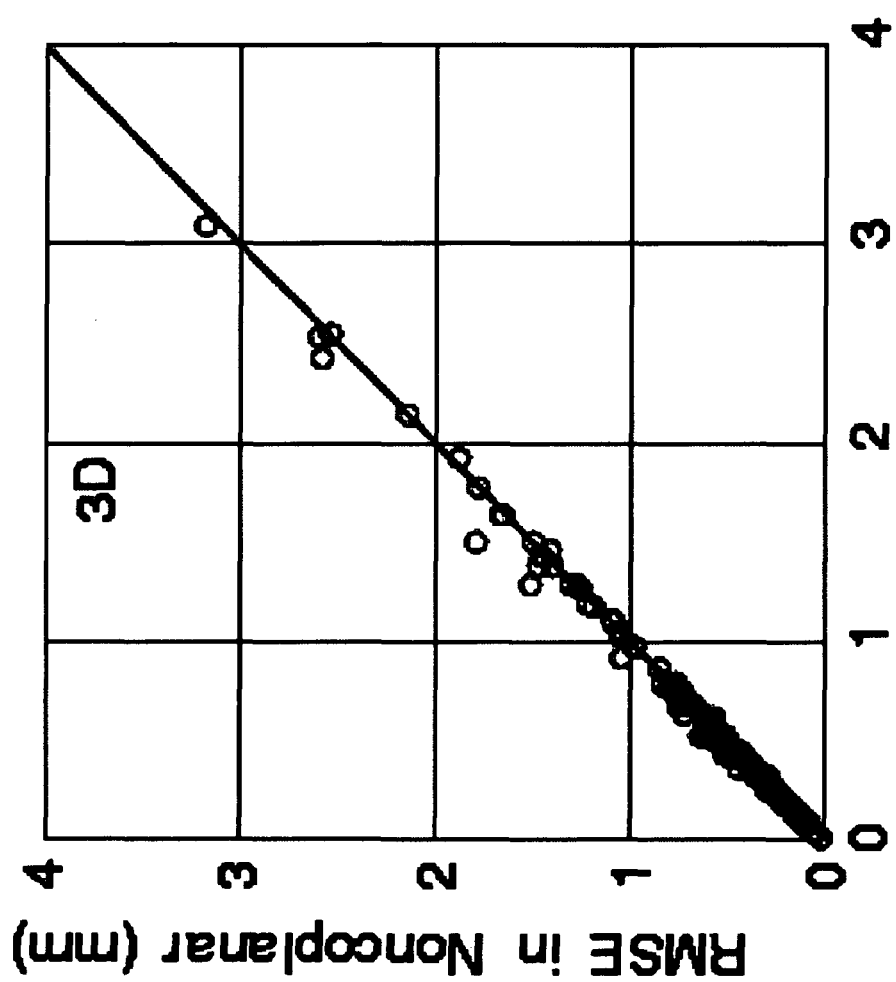
FIGS. 7a-7d show the sequential image-based estimation for the alternate stereoscopic imaging in the coplanar versus non-coplanar geometry at the 1 s interval, according to one embodiment of the invention.
Figure 7:
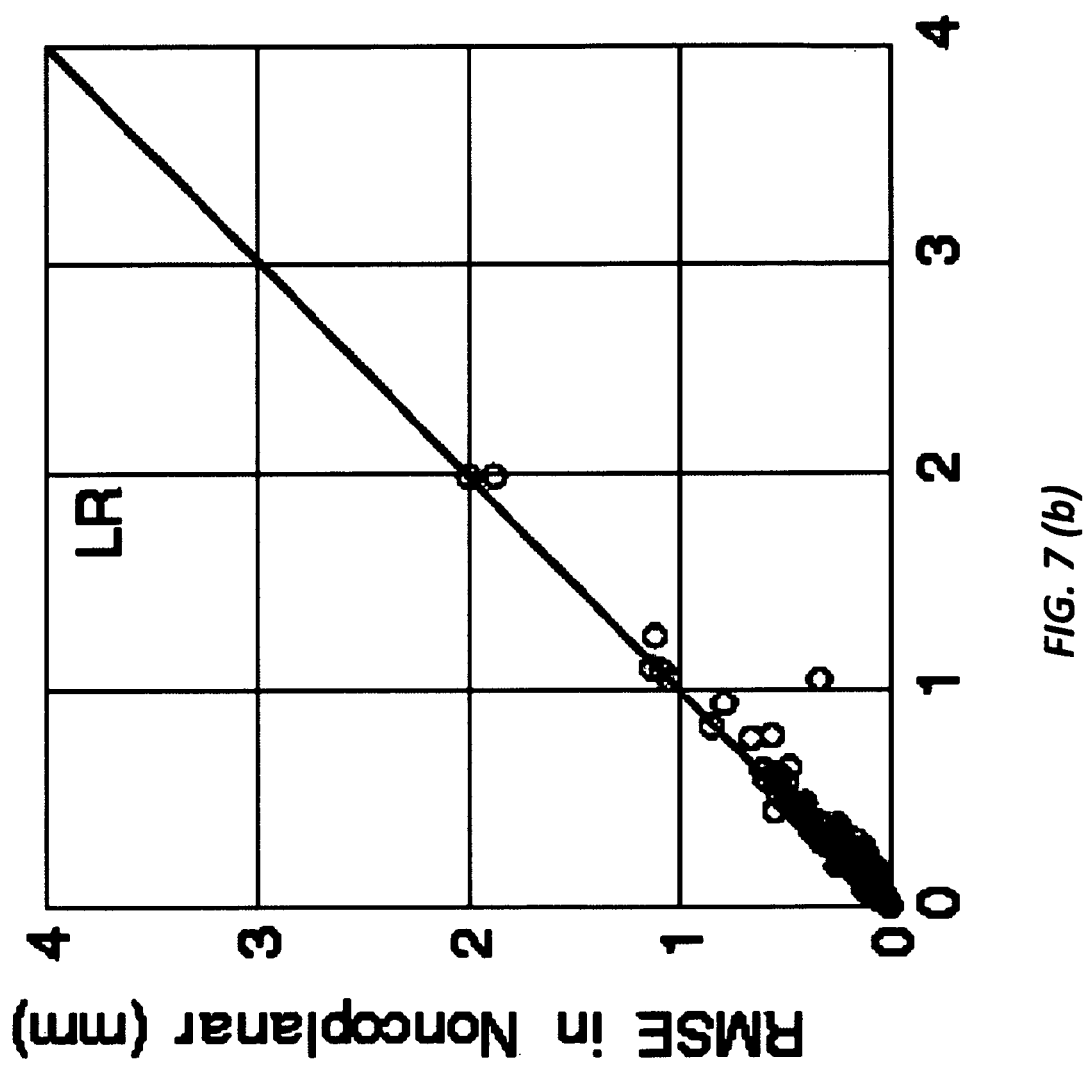
Figure 7C:
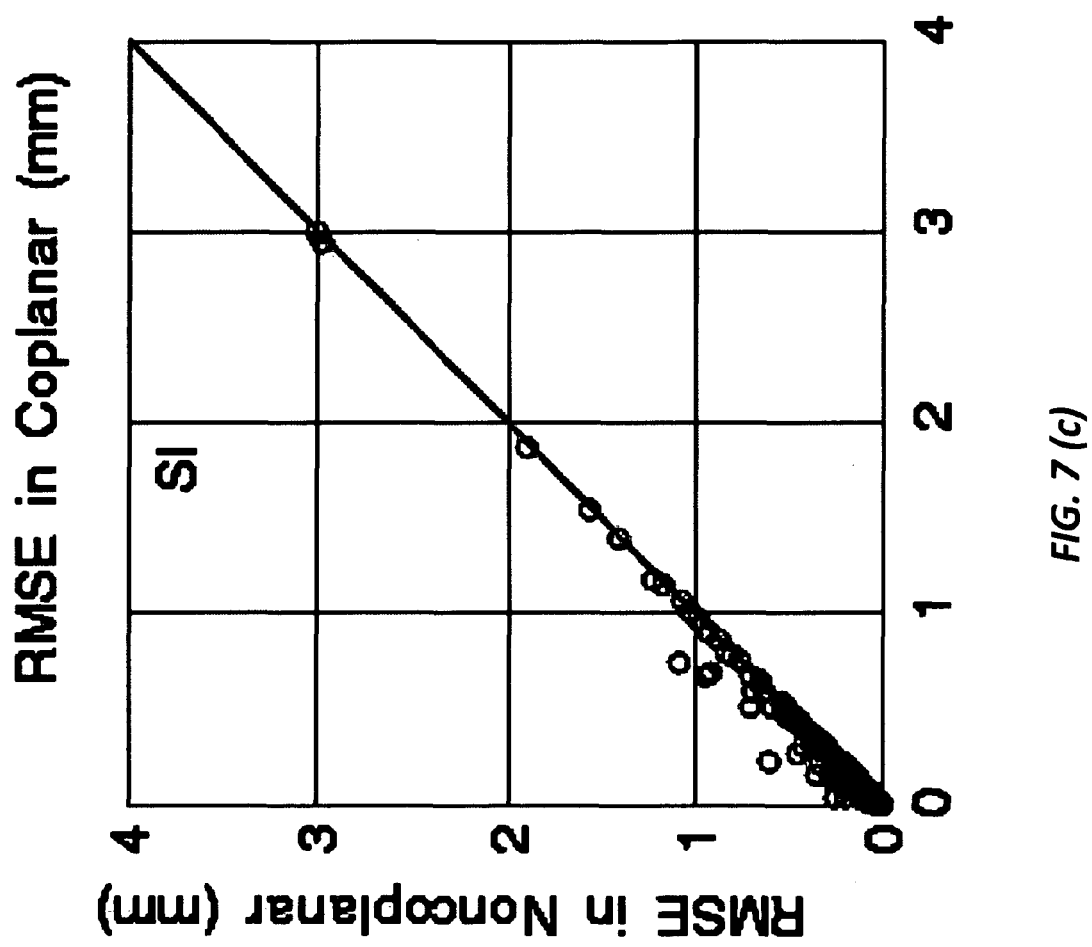
Figure 7D:
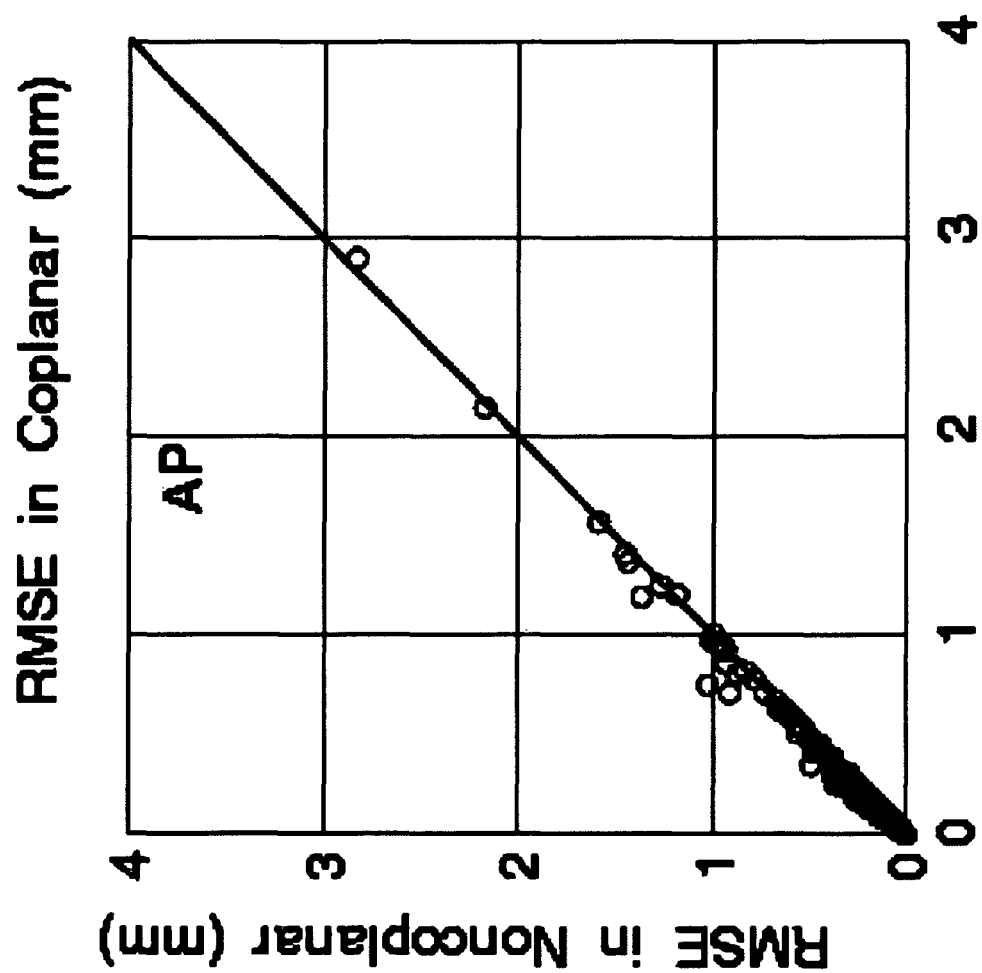

The sequential image-based estimation for the alternate stereoscopic imaging in the coplanar and non-coplanar geometries was simulated at various imaging intervals. FIGS. 7a-7b show the coplanar versus non-coplanar pair-wise comparisons of the estimation errors over the 160 dataset for the 1 s imaging interval. The SI component was always resolved in the coplanar geometry, but not in the non-coplanar geometry. Thus the estimation of the SI component is more accurate in the coplanar geometry than in the non-coplanar geometry. On the other hand, the estimation of the LR(x) component would be more accurate in the non-coplanar geometry since $y_p$ also shares the LR information. Likewise, the AP(z) component is more accurate in the coplanar geometry because it is estimated from $x_p = \cos\theta \cdot T_x + \sin\theta \cdot T_z$ compared to the non-coplanar geometry, where $x_p$ is the combination of all three patient coordinates. Overall the coplanar geometry is more favorable to the sequential image-based estimation because the AP and SI, which are known as relatively large components of respiratory motion, can be estimated more accurately, resulting in better accuracy. However the accuracy improvement is less than 0.01 mm in the overall 3D RMSE.

As for the SAD dependence of the estimation accuracy in the sequential image-based estimation, larger SAD is expected to be more favorable to the sequential image-based estimation because in the perspective term it becomes closer to parallel projection and results in smaller error in equation (8). As SAD was increased from 100 to 250 cm, the average RMSE over the 160 trajectories was improved by only 0.02% for the rotational monoscopic imaging at the 1 s interval.

Figure 8:
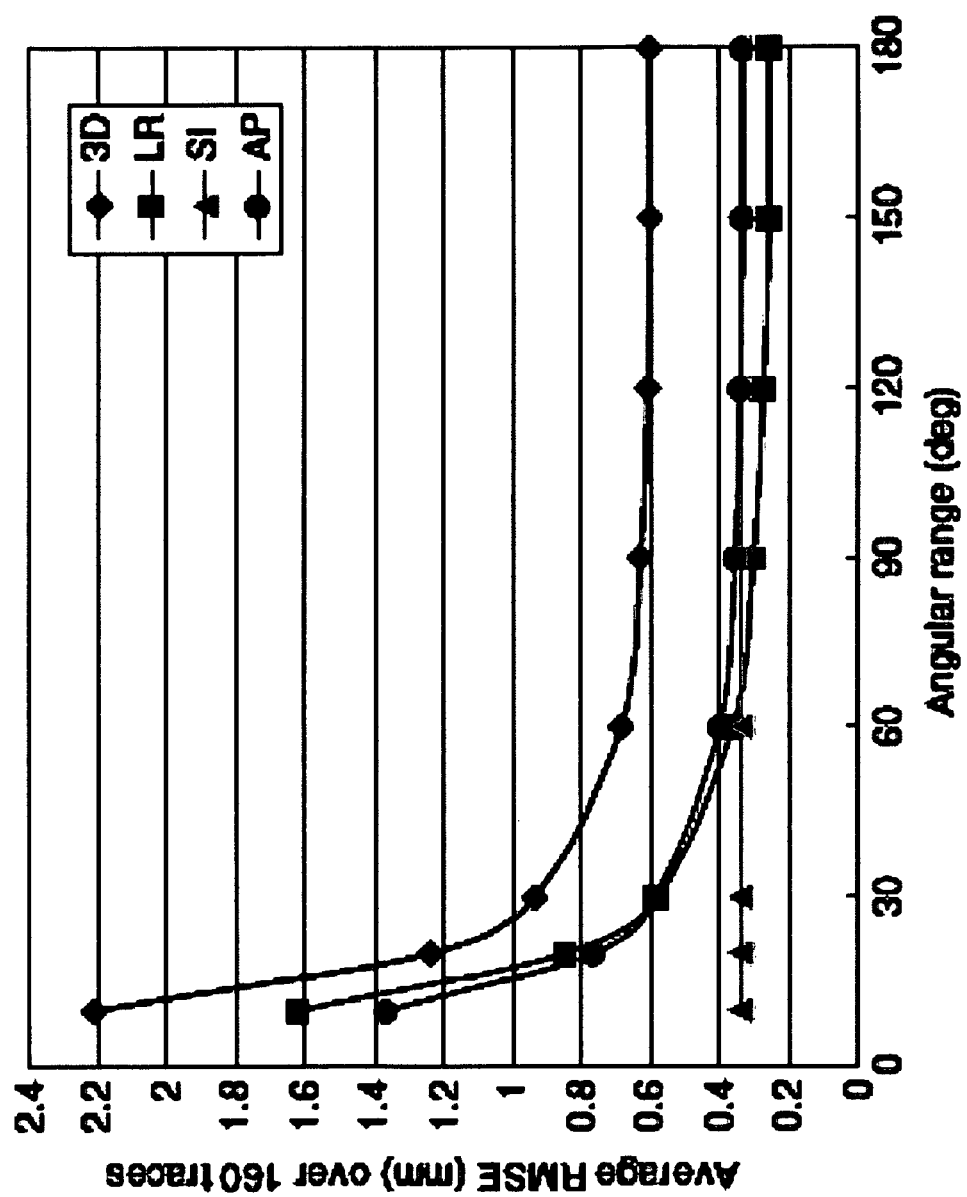
FIG. 8 shows simulating the sequential image-based estimation for the rotational monoscopic imaging in the coplanar geometry as a function of the angular span, according to one embodiment of the current invention.

The effect of the angular span on the estimation accuracy is provided by simulating the sequential image-based estimation for the rotational monoscopic imaging in the coplanar geometry as a function of the angular span. The results are shown in FIG. 8. As the angular span narrowed from 180° to 120°, there was little loss of estimation accuracy. Note that an angular span of 120° corresponds to a 6° angular separation between consecutive images and an average angular separation of images of 60°. The mean 3D estimation error increased around 5% and 14% at 90° and 60° angular span, respectively. After that, it increased rapidly with further narrowing of the angular span. As expected, the estimation error in the resolved SI direction was irrelevant to the angular span. The errors in both the LR and AP directions increased together because of rotational imaging.

In the limit when the angular span narrowed down to zero, the sequential image-based estimation became singular. To make it solvable further constraint on the correlation model should be imposed. The correlation is modeled in the imager plane as $$\begin{pmatrix} x_p \\ y_p \end{pmatrix} = \begin{pmatrix} a_x \\ a_y \end{pmatrix} R + \begin{pmatrix} b_x \\ b_y \end{pmatrix},$$

and the further constraint in the unresolved motion is imposed as $\hat{z}' = a_z x_p + b_z y_p + c_z$ with a priori 3D target motion information. Since the correlation model itself is affixed to the imager coordinates, it should be reset and re-built whenever the beam direction is changed. When reformulated in the patient coordinates with an inter-dimensional relationship, $\hat{x} = ay + bz + c$, this problem is merged into the framework of the sequential image-based estimation, according to the current invention. Moreover, the parameters of the inter-dimensional relationship, i.e. a priori 3D target motion information, can be obtained naturally with the rotational monoscopic imaging.

In an approach employing an inter-dimensional correlation model in the imager coordinates for kV/MV image-based tracking without an external respiratory monitor, the same framework can also be applied to this approach, with the inter-dimensional correlation expressed in the patient coordinates such as $x = ay + bz + c$. Here, it would eliminate the need for rebuilding the model parameters with changes in the beam direction and provide a natural way to build the correlation for rotational imaging.

The internal-external correlation model is aimed at estimating respiratory tumor motion using external breathing monitors, and thus is not feasible for tumor motion irrelevant to breathing (such as prostate). On the other hand, position estimation methods using x-ray imaging alone require a fairly fast imaging frequency to obtain real-time estimation of a moving tumor. Thus both methods can be used complementarily depending on the purpose of the applications, treatment sites and clinical needs.

Finally, though the current invention focuses on kV imaging due to improved contrast and noninterference of MLC leaves, without loss of generality the method could be applied to MV imaging systems alone or in combination with kV imaging.

According to the current invention, a generalized 3D target position estimation method based on internal-external correlation has been developed and investigated. The key idea of the sequential image-based estimation is (1) recasting the least-squares formula for estimating the correlation model parameters from expressions in the patient coordinates to expressions in the projection coordinates, and (2) further reformulation of the model in a quickly-converging iterative form supported by the fact that the perspective projection in the range of tumor motion is nearly a parallel projection. The method was verified in a large dataset through simulations for a variety of common clinical IGRT configurations: synchronous stereoscopic imaging, alternate stereoscopic imaging, and rotational monoscopic imaging. The accuracy of the method was similar for all of the clinical configurations. The estimation accuracy showed mean 3D RMSE less than 1 mm and had a weak dependence on imaging frequency. Most importantly, the estimation accuracy of the sequential image-based estimation was the same as the synchronous stereoscopic image-based estimation for the same synchronously acquired stereoscopic images. The practical significance of this fact is that with the sequential image-based estimation the alternate stereoscopic and rotational monoscopic imaging systems can achieve the same accuracy for the correlation-based 3D target position estimation as the synchronous stereoscopic imaging systems for the same imaging dose to the patient. The sequential image-based estimation method of the current invention is applicable to all common IGRT systems and could overcome some limitations of synchronous stereoscopic imaging systems, such as when the linac obscures one of the x-ray systems.

According to one aspect, the invention applies to an online adaptive imaging method and system for reducing diagnostic radiation dose in image guided radiotherapy, which can account for accumulative effect of imaging dose and treatment dose in IGRT and use adaptive imaging to minimize radiation toxicity without compromising delivery accuracy.

According to this aspect, a global optimality metric in dose delivery is formulated systematically that accounts for the accumulative effect of diagnostic radiation and treatment radiation. Utilizing the observation that the region affected by imaging radiation is almost complementary to the treatment plan and delivery, where treating the imaging dose as a "cost" that should be controlled avoids tissue toxicity during image guided radiotherapy. Combined with a probabilistic prediction algorithm with hybrid (multimodality) inputs that compensates for system latency, an online adaptive imaging system is devised so that radiographic images are only taken when the instantaneous geometric and topological estimate suffers from high uncertainty. The objective in the optimization setup is formulated in terms of dose difference, and reflects clinical endpoint. Parameters for controlling dose per image and instances for imaging acquisition are optimized with respect to the defined objective. Retrospective optimization is found to be closely associated with a typical resource allocation, where provided is a solution analogous to the classic "reverse water filling" scheme. The online optimization scheme is formulated and efficiently solved in a dynamic programming framework.

This aspect of the invention is the first method/system that explicitly accounts for the combined effect of diagnostic dose and treatment dose. Adaptive imaging based on estimation accuracy provides quality assurance uniformly on the delivery efficacy throughout the whole duration of treatment. It realizes the core principles in radiation imaging "as low as reasonably achievable" with ensured delivery accuracy. This aspect allows extension to hybrid (multimodality) inputs, including optical reading, kV/MV imaging. It is also compatible with various prediction options, as long as the predictor provides simultaneously an estimate of the state and the associated error/uncertainty.

Even though the philosophy that diagnostic dose should be accounted for in planning and treatment is widely recognized, this is the first system that embodies such principle in system design and online optimization. The clinical endpoint aligned optimization, the interpretation in terms of resource allocation (both offline and online), and the corresponding solutions are all novel components. This embodiment provides instantaneous online decisions on imaging excitation, flux level, imager configuration parameters and provides the corresponding expected dose deviation from such scheme. In motion-adaptive IGRT, the current embodiment improves the agreement between planned dose pattern and delivery result, and reduces the likelihood of tissue toxicity.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of estimating target motion for image guided radiotherapy (IGRT) systems, comprising:
    a. acquiring by a kV imaging system sequential images of a target motion;
    b. computing by said kV imaging system from said sequential images an image-based estimation of said target motion expressed in a patient coordinate system;
    c. transforming by said kV imaging system said image-based estimation in said patient coordinate system to an estimate in a projection coordinate system;
    d. reformulating by said kV imaging system said projection coordinate system in a converging iterative form to force a convergence of said projection coordinate system to output a resolved estimation of said target motion; and
    e. displaying by said kV imaging system said resolved estimation of said target motion.

2. The method of claim 1, wherein said target position T(x, y, z) comprises an x-direction corresponding to a left-right (LR) orientation in said patient coordinate system, a y-direction corresponding to a superior-inferior (SI) orientation in said patient coordinate system, and a z-direction corresponding to an anterior-posterior (AP) orientation in said patient coordinate system.

3. The method of claim 1, wherein said imaging coordinate system comprises a kV source located at a kV source to axis distance (SAD), wherein said axis is a target isocenter, and an imager located at said SAD minus a source to imager distance (SID), wherein an origin of said imaging coordinate system is coincident with said target isocenter.

4. The method of claim 1, wherein said kV imaging system is selected from the group consisting of an alternate stereoscopic sequential imaging system, a rotational monoscopic sequential imaging system, and a synchronous stereoscopic imaging system.

5. The method of claim 1, wherein said transforming said image-based estimation in said patient coordinate system to an estimate in a projection coordinate system comprises:
    a. sequentially applying a counter-clock wise rotation $\phi$ about the z-axis in said patient coordinate system and rotation of $\theta$ around the y-axis in said patient coordinate system;
    b. applying a projection into the z' direction of the imager coordinate system; and
    c. performing a least squares estimate in said projection coordinate system using said suitably programmed computer.

6. The method of claim 1, transforming said image-based estimation in said patient coordinate system to an estimate in a projection coordinate system comprises reformulating a least-squares estimation of target-surrogate model parameters from expressions in said patient coordinates to expressions in said projection coordinates.

7. The method of claim 1, wherein said target position T(x, y, z) is continuously estimated using a signal R through the correlation between sequential signals $R_i$ and projected marker positions $p_i$ on intermittently acquired kV images, wherein said signal R is generated by optical respiratory sensors or accelerometers.

* * * * *

UNITED STATES PATENT AND TRADEMARK OFFICE
CERTIFICATE OF CORRECTION

PATENT NO.       : 8,396,270 B2                     Page 1 of 1
APPLICATION NO.  : 12/932060
DATED            : March 12, 2013
INVENTOR(S)      : Paul J. Keall et al.

It is certified that error appears in the above-identified patent and that said Letters Patent is hereby corrected as shown below:

In The Specification

Please correct the following paragraph starting in Column 1, line 14, from:

STATEMENT OF GOVERNMENT SPONSORED SUPPORT
This invention was made with Government support under contract NIH/NCI R01 93626 awarded by National Institutes of Health/National Cancer Institute. The Government has certain rights in this invention.

into:

STATEMENT OF GOVERNMENT SPONSORED SUPPORT
This invention was made with Government support under contract CA093626 awarded by the National Institutes of Health. The Government has certain rights in the invention.

Signed and Sealed this
Twenty-ninth Day of March, 2016

Michelle K. Lee
*Director of the United States Patent and Trademark Office*